United States Patent
Messersmith et al.

(10) Patent No.: US 9,320,719 B2
(45) Date of Patent: Apr. 26, 2016

(54) MULTIFUNCTIONAL METAL NANOPARTICLES HAVING A POLYDOPAMINE-BASED SURFACE AND METHODS OF MAKING AND USING THE SAME

(71) Applicants: Phillip B. Messersmith, Clarendon Hills, IL (US); Kvar C. L. Black, IV, Evanston, IL (US); Ji Yi, Evanston, IL (US); Jose G. Rivera, Waukegan, IL (US)

(72) Inventors: Phillip B. Messersmith, Clarendon Hills, IL (US); Kvar C. L. Black, IV, Evanston, IL (US); Ji Yi, Evanston, IL (US); Jose G. Rivera, Waukegan, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/294,636

(22) Filed: Jun. 3, 2014

(65) Prior Publication Data

US 2014/0271889 A1    Sep. 18, 2014

Related U.S. Application Data

(62) Division of application No. 13/420,189, filed on Mar. 14, 2012, now Pat. No. 8,784,895.

(60) Provisional application No. 61/453,054, filed on Mar. 15, 2011.

(51) Int. Cl.
| | | |
|---|---|---|
| A61K 9/51 | (2006.01) | |
| A61N 5/06 | (2006.01) | |
| G01N 33/58 | (2006.01) | |
| A61K 41/00 | (2006.01) | |
| A61K 39/395 | (2006.01) | |
| A61K 9/00 | (2006.01) | |
| A61K 9/50 | (2006.01) | |
| A61K 47/48 | (2006.01) | |
| A61K 49/18 | (2006.01) | |
| B82Y 5/00 | (2011.01) | |
| C07K 16/00 | (2006.01) | |
| G01N 21/47 | (2006.01) | |
| G01N 21/552 | (2014.01) | |
| A61K 31/69 | (2006.01) | |
| A61K 33/00 | (2006.01) | |
| B82Y 40/00 | (2011.01) | |
| A61K 45/06 | (2006.01) | |
| A61K 33/26 | (2006.01) | |
| A61K 33/38 | (2006.01) | |
| A61K 39/40 | (2006.01) | |

(52) U.S. Cl.
CPC ............... *A61K 9/51* (2013.01); *A61K 9/0092* (2013.01); *A61K 9/5094* (2013.01); *A61K 31/69* (2013.01); *A61K 33/00* (2013.01); *A61K 33/26* (2013.01); *A61K 33/38* (2013.01); *A61K 39/39558* (2013.01); *A61K 39/40* (2013.01); *A61K 41/0052* (2013.01); *A61K 41/0057* (2013.01); *A61K 45/06* (2013.01); *A61K 47/48861* (2013.01); *A61K 49/1857* (2013.01); *A61N 5/062* (2013.01); *B82Y 5/00* (2013.01); *B82Y 40/00* (2013.01); *C07K 16/00* (2013.01); *G01N 21/4795* (2013.01); *G01N 21/554* (2013.01); *G01N 33/587* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally et al. | 424/450 |
| 6,428,811 B1 | 8/2002 | West et al. | |
| 6,530,944 B2 | 3/2003 | West et al. | |
| 7,610,074 B2 | 10/2009 | Boppart et al. | |
| 7,622,533 B2 | 11/2009 | Lee | |
| 2003/0087338 A1 | 5/2003 | Messersmith et al. | |
| 2005/0175584 A1 | 8/2005 | Paciotti et al. | |
| 2008/0003183 A1 | 1/2008 | Guo | |
| 2008/0149566 A1 | 6/2008 | Messersmith et al. | |
| 2009/0326614 A1 | 12/2009 | El-Sayed et al. | |

FOREIGN PATENT DOCUMENTS

WO    2006122222 A2    11/2006

OTHER PUBLICATIONS

Christiansen et al (Mol Cancer Ther, 2004, 3:1493-1501).*
Topp et al (Journal of Controlled Release, 1998, 53:15-23).*
Vajdos et al. (J Mol Biol. Jul. 5, 2002;320(2):415-28.*
Brown et al. (J Immunol. May 1996;156(9):3285-91 at 3290 and Tables 1 and 2).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*

(Continued)

*Primary Examiner* — Brian J Gangle
*Assistant Examiner* — Andrea McCollum
(74) *Attorney, Agent, or Firm* — Quarles & Brady, LLP

(57) ABSTRACT

The present invention provides nanoparticles including a metallic core having a length along each axis of from 1 to 100 nanometers and a coating disposed on at least part of the surface of the metallic core, wherein the coating comprises polydopamine, along with methods for making and using such nanoparticles. The metallic core may be gold, silver or iron oxide and the polydopamine coating may have other substances bound to it, such as silver, targeting ligands or antibodies, or other therapeutic or imaging contrast agents. The disclosed nanoparticles can be targeted to cells for treating cancer or bacterial infections, and for use in diagnostic imaging.

5 Claims, 32 Drawing Sheets

(56) References Cited

OTHER PUBLICATIONS

Aslan, et al., Plasmon Light Scattering in Biology and Medicine: New Sensing Approaches, Visions and Perspectives, Current Opinion in Chemical Biology, 2005, 9(5):538-544.
Black, et al., Gold Nanorods Targeted to Delta Opioid Receptor: Plasmon-Resonant Contrast and Photothermal Agents, Mol. Imaging, 2008, 7(1):50-57.
Chen, et al., Gold Nanocages: Bioconjugation and Their Potential Use as Optical Imaging Contrast Agents, Nano Lett., 2005, 5(3):473-477.
El-Sayed, et al., Surface Plasmon Resonance Scattering and Absorption of Anti-EGFR Antibody Conjugated Gold Nanoparticles in Cancer Diagnostics: Applications in Oral Cancer, Nano Lett., 2005, 5(5):829-834.
Huang, et al., Synthesis and Characterization of Au core-Au—Ag Shell Nanoparticles from Gold Seeds: Impacts of Glycine Concentration and pH, Journal of Colloid and Interface Science, 2006, 301(1):145-154.
Huff, et al., Hyperthermic Effects of Gold Nanorods on Tumor Cells, Nanomedicine, 2007, 2(1):125-132.
Jain, et al., Noble Metals on the Nanoscale: Optical and Photothermal Properties and Some Applications in Imaging, Sensing, Biology and Medicine, Acc. Chem. Res., 2008, 41(12):1578-1586.
Jana, et al., Wet Chemical Synthesis of High Aspect Ratio Cylindrical Gold Nanorods, J. Phys. Chem. B, 2001, 105 (19):4065-4067.
Lal, et al., Nanoshell-Enabled Photothermal Cancer Therapy: Impending Clinical Impact, Acc. Chem. Res., 2008, 41 (12):1842-1851.
Lee, et al., Mussel-Inspired Surface Chemistry for Multifunctional Coatings, Science, 2007, 318(5849):426-430.
Liu, et al., Synthesis and Optical Characterization of Au/Ag Core/Shell Nanorods, J. Phys. Chem. B, 2004, 108 (19):5882-5888.
Mirkin, et al., A DNA-Based Method for Rationally Assembling Nanoparticles Into Macroscopic Materials, Nature, 1996, 382:607-609.
Norman, et al., Targeted Photothermal Lysis of the Pathogenic Bacteria, *Pseudomonas Aeruginosa*, With Gold Nanorods, Nano Lett., 2008, 8(1):302-306.
Sun, et al., Gold and Silver Nanoparticles: A Class of Chromophores with Colors Tunable in the Range from 400 to 750 nm, Analyst, 2003, 128:686-691.
Sun, et al., Heparin-Coated Gold Nanoparticles for Liver-Specific CT Imaging, Chem. Eur. J., 2009, 15:13341-13347.
Tong, et al., Gold Nanorods as Contrast Agents for Biological Imaging: Optical Properties, Surface Conjugation and Photothermal Effects, Photochemistry and Photobiology, 2009, 85:21-32.
Turkevich, et al., A Study of the Nucleation and Growth Processes in the Synthesis of Colloidal Gold, Discuss. Faraday Soc., 1951, 11:55-75.
Wolfe, et al., Photodeposition of Molecular Layers on Nanoparticle Substrates, Langmuir, 1999, 15(8):2745-2748.
Xie, et al., Silver Nanoplates: From Biological to Biomimetic Synthesis, ACS Nano, 2007, 1(5):429-439.
Cui, et al., Monodisperse Polymer Capsules: Tailoring Size, Shell Thickness, and Hydrophobic Cargo Loading Via Emulsion Templating, Adv. Funct. Mater., 2010, 20:1625-1631.
Fu, et al., Novel Polymeric Bionanocomposites with Catalytic Pt Nanoparticles Label Immobilized for High Performance Amperometric Immunoassay, Biosensors and Bioelectronics, 2010, 25:1699-1704.
Lai, et al., Surface Functionalization of TiO2 Nanotubes with Bone Morphogenetic Protein 2 and Its Synergistic Effect on the Differentiation of Mesenchymal Stem Cells, Biomacromolecules, 2011, 12(4):1097-1105.
Lynge, et al., Polydopamine—a Nature-Inspired Polymer Coating for Biomedical Science, Nanoscale, 2011, 3:4916-4928.
Si, et al., Preparation and Characterization of Bio-Compatible Fe3O4@Polydopamine Spheres with Core/Shell Nanostructure, Materials Chemistry and Physics, 2011, 128:519-524.
Sureshkumar, et al., Polydopamine Coated Magnetic-Chitin (MCT) Particles as a New Matrix for Enzyme Immobilization, Carbohydrate Polymers, 2011, 84:775-780.
Wang, et al., Dual Functional Electrochemical Sensor Based on Au-polydopamine-Fe3O4 Nanocomposites, Anal. Methods., 2011, 3:2475-2477.
Yu, et al., Robust Polydopamine Nano/Microcapsules and Their Loading and Release Behavior, Chem. Commun., 2009, 44:6789-6791.
Yu, et al., Pdop Layer Exhibiting Zwitterionicity: A Simple Electrochemical Interface for Governing Ion Permeability, Chem. Commun., 2010, 46:5900-5902.
Zhang, M., et al., Preparation and Characterization of Polydopamine-coated Silver Core/Shell Nanocables, Chemistry Letters, 2010, 39(6):552-553.
Zhang, M., et al., Preparation of IDA-Cu Functionalized Core-Satellite Fe3O4/polydopamine/Au Magnetic Nanocomposites and Their Application for Depletion of Abundant Protein in Bovine Blood, Journal of Materials Chemistry, 2010, 20:10696-10704.
Zhang, Y., et al., Mussel-Inspired Fabrication of Encoded Polymer Films for Electrochemical Identification, Electrochemistry Communications, 2009, 11:1936-1939.
Zhou, et al., Mussle-inspired Molecularly Imprinted Polymer Coating Superparamagnetic Nanoparticles for Protein Recognition, Journal of Materials Chemistry, 2010, 20:880-883.
PCT International Search Report and Written Opinion, PCT/US2012/029023, Oct. 5, 2012.
Sokolov et al. Real-time vital optical imaging of precancer using anti-epidermal growth factor receptor antibody. Cancer Res. May 1, 2003; 63(9): 1999-2004.

\* cited by examiner (a)

(b)

MULTIFUNCTIONAL METAL NANOPARTICLES HAVING A POLYDOPAMINE-BASED SURFACE AND METHODS OF MAKING AND USING THE SAME

CROSS-REFERENCE TO RELATED APPLICATIONS

This application is a divisional of U.S. patent application Ser. No. 13/420,189, filed Mar. 14, 2012 and claims the benefit of U.S. Provisional Application No. 61/453,054, filed on Mar. 15, 2011, both of which are incorporated by reference herein in their entirety for all purposes.

STATEMENT REGARDING FEDERALLY SPONSORED RESEARCH OR DEVELOPMENT

This invention was made with government support under Grant Numbers R43 DE014193, F31 DE019750, and R01 EB005772-01 A2 awarded by the National Institutes of Health. The government has certain rights in the invention.

FIELD OF THE INVENTION

This disclosure relates generally to metal nanoparticles that are surface-coated with polydopamine. In addition, the disclosure encompasses methods of making such nanoparticles and methods for using such nanoparticles in medical diagnosis and treatment.

BACKGROUND OF THE INVENTION

Metal nanoparticles (NPs) have a long history of use dating back to the $4^{th}$ or $5^{th}$ century B.C.E. The optical properties of conductive gold and silver NPs have been associated with the surface plasmon resonance (SPR) of metals, which when confined to small colloids, is referred to as the localized surface plasmon resonance (LSPR). This phenomenon, in which the free electrons oscillate collectively on the metal surface when irradiated with particular energies of light, causes wavelength dependent absorption and scattering of light and is the source of the colors associated with metal nanoparticles. The size, shape, and composition of the colloidal particles determines the energy of the SPRs, and therefore, control over the synthesis of metal NPs provides an ability to tune the optical properties of the nanometals contained therein.

Since Turkevich et al. first described the synthesis of metal nanoparticles by reduction of cationic noble metal ions in solution (*Discuss. Faraday Soc.* 11 (1951): 55), colloidal suspensions of various NP morphologies have been accomplished, including gold-silver alloys (Y. Sun et al., *Analyst* 128 (2003): 686-691), core-shell NPs (D. B. Wolfe et al., *Langmiur* 15 (1999): 2745), gold nanorods (NRs) (N. R. Jana et al., *J. Phys. Chem. B* 105(19) (2001): 4065-4067), silver nanosheets (J. Xie et al., *ACS nano* 1(5) (2008): 429-439, and gold nanocages (J. Chen et al., *Nano Lett.* 5(3) (2005): 473-477). Hybrid approaches such as silver-shell gold NR core NPs have also been employed (M. Lui et al., *J. Phys. Chem. B* 108 (2004): 5882-5888).

Surface plasmon resonant metal nanoparticles have broad potential in medical diagnostic and therapeutic applications, due to their relative inertness, sub-100 nm size, unique electromagnetic properties, and strong optical tunability. Accordingly, metal NPs have attracted attention in the biomedical field. For example, linking DNA to gold NPs allows biological interactions to form assemblies of colloidal clusters that change the optical properties of the suspension (C. A. Mirkin et al., *Nature* 382 (1996): 607-609), which can be detected for diagnostic purposes. Because SPRs enhance many optical processes, including Raman scattering, fluorescence, and two-photon excited luminescence, gold NPs have been used in optical diagnostics (K. Asian et al., *Current Opinion in Chemical Biology* 9 (2005): 538-544) and as contrast agents for bioimaging (I. H. EI-Sayed et al., *Nano Letters* 5(5) (2005): 829-834; K. C. Black et al., *Mol. Imaging* 7(1) (2008): 50-57). When gold NPs absorb light energy, they also release heat, potentially making them useful in photothermal therapy applications targeting cancer (T. B. Huff et al, *Nanomedicine* 2(1) (2007): 125-132) and bacterial cells (S. E. Norman et al., *Nano letters* 8(1) (2008): 302-306.

However, the use of metal NPs for medical diagnosis and treatment is limited, because NPs cannot be fully integrated into the biological realm without tailored control over their surface chemistry. Biomolecules and cells interact through a multitude of chemical interactions and physical forces which have not evolved in the presence of noble metals, and therefore interactions between biological systems and metal NPs are non-specific. In order to realize the full biomedical potential of gold nanoparticles, the nanoparticles must interact specifically with biological matter, including cell surface components. Furthermore, nanoparticle aggregation and non-specific interactions with molecular and cellular constituents of the biological system must be minimized. Thus, there is a need in the art for metal nanoparticles that can be readily modified to precisely control their electromagnetic and biofunctional properties.

SUMMARY OF THE INVENTION

The disclosure encompasses novel metal nanoparticles having polydopamine polymerized onto the nanoparticle surface. In some embodiments, the surface is modified further in a variety of ways. Non-limiting examples of the function of such further modifications include modulating toxicity, controlling the conversion of light energy to heat energy, inhibiting non-specific interactions, increasing solubility in physiological conditions, providing pro-apoptotic function, providing specific targeting, and providing growth factor pathway inhibition.

Accordingly, in a first aspect, the disclosure encompasses nanoparticles that includes a metallic core having a length along each axis of from 1 to 100 nanometers, and a polydopamine coating disposed on at least part of the surface of the metallic core. In some embodiments, the metallic core is a nanorod having a substantially cylindrical shape. In some embodiments, the polydopamine coating is disposed on the entire surface of the metallic core. In some embodiments, the metallic core includes gold, and optionally, may consist essentially of gold.

The polydopamine coating may be modified in a number of ways, depending on the desired function of the nanoparticles. For example, in some embodiments the coating may further include silver. In some embodiments, the coating may further include iron oxide. In some embodiments, the nanoparticles further include one or more polymers, polysaccharides, sugar-containing peptoids, pharmaceutical agents, antibodies, polyethylene glycol, or a functionalized polyethylene glycol bound to the coating. Optionally, one or more of the bound antibodies is an anti-cancer cell surface receptor antibody or an anti-bacterial surface antibody. Optionally, one or more of the bound pharmaceutical agents is an anti-cancer agent or an antimicrobial agent.

In a second aspect, the disclosure encompasses a method of making the nanoparticles described above. The method includes the step of contacting a metallic core having a length along each axis of from 1 to 100 nanometers with an alkaline solution comprising dopamine. This step results in the formation of a polydopamine coating on the surface of the metallic core. In some embodiments, the metallic core is a nanorod having a substantially cylindrical shape. In some embodiments, the metallic core consists essentially of gold.

In a third aspect, the disclosure encompasses a method for treating cancer. The method includes the step of administering to a patient having cancer cells one or more of the nanoparticles that are described above. In some embodiments, the metallic core consists essentially of gold, and one or more anti-cancer cell surface receptor antibodies are bound to the polydopamine coating of the nanoparticles. The antibodies cause the nanoparticles to target the cancer cells. A non-limiting example of an antibody that could be bound to the coating of the nanoparticles to target cancer cells is an anti-epithelial growth factor receptor (EGFR) antibody.

In some embodiments, the nanoparticles may further include an additional anti-cancer agent bound to the polydopamine coating. A non-limiting example of such an anti-cancer agent is a proteasome inhibitor, such as bortezomib.

In some embodiments, the method further includes the step of exposing the nanoparticles to light. Upon such exposure, the nanoparticles heat up, and the resulting photothermal therapy differentially kills the targeted cells.

In a fourth aspect, the disclosure encompasses a method for treating a bacterial infection. The method includes the step of administering to a patient infected with bacteria one or more of the nanoparticles described above that include a metallic core consisting essentially of gold and an anti-bacterial surface antibody bound to the polydopamine coating. The nanoparticles then target the bacteria that is the source of the infection.

Optionally, the anti-bacterial surface antibody is an anti-lipoteichoic acid antibody or an anti-endotoxin antibody. In some embodiments, the polydopamine coating further incorporates a layer of silver. In some embodiments, the method further includes the step of exposing the nanoparticles to light.

In a fifth aspect, the disclosure encompasses a method for imaging cancer or bacterial cells. The method includes the steps of contacting cancer or bacterial cells with one or more of the nanoparticles described above, wherein the metallic core consists essentially of gold and wherein the nanoparticles include an anti-cancer cell surface receptor antibody or an anti-bacterial surface antibody bound to the polydopamine coating. The antibody functions as a targeting agent so that the nanoparticles target the cancer or bacterial cells.

The method also includes the step of detecting the location of the one or more nanoparticles. Optionally, this step may be performed using bright field microscopy, optical coherence tomography, or 2-photon confocal microscopy. In some embodiments, the nanoparticle coating further comprises iron oxide, and the step of detecting the location of the one or more nanoparticles is performed using magnetic-based imaging.

Further objects, features and advantages of the invention will be apparent from the following detailed description when taken in conjunction with the accompanying drawings.

BRIEF DESCRIPTION OF THE DRAWINGS

FIG. 3(c) shows the movement of the these conjugates with an external magnet, and FIG. 3(d) shows their optical spectrum in suspension after movement with the magnet and subsequent resuspension.

FIG. 7(c) shows quantitative cell viability determined from cell images.

FIG. 9(b) Antibody density as a function of concentration of antibody added to $3.62 \times 10^{13}$ NR/L.

FIG. 13 (a) shows survey scans and FIG. 13 (b) shows high resolution C1s scans of (top) CTAB-NRs and (bottom) PD-NRs.

cells incubated for 1.5 hours with 9.92 pM anti-EGFR-PD-NRs with no irradiation; (c) cells incubated for 1.5 hours with 9.92 pM PEG-PD-NRs and irradiated for 5 minutes, (d) cells treated with 9.92 pM anti-EGFR-PD-NRs and irradiated for 5 minutes.

Figure 17:
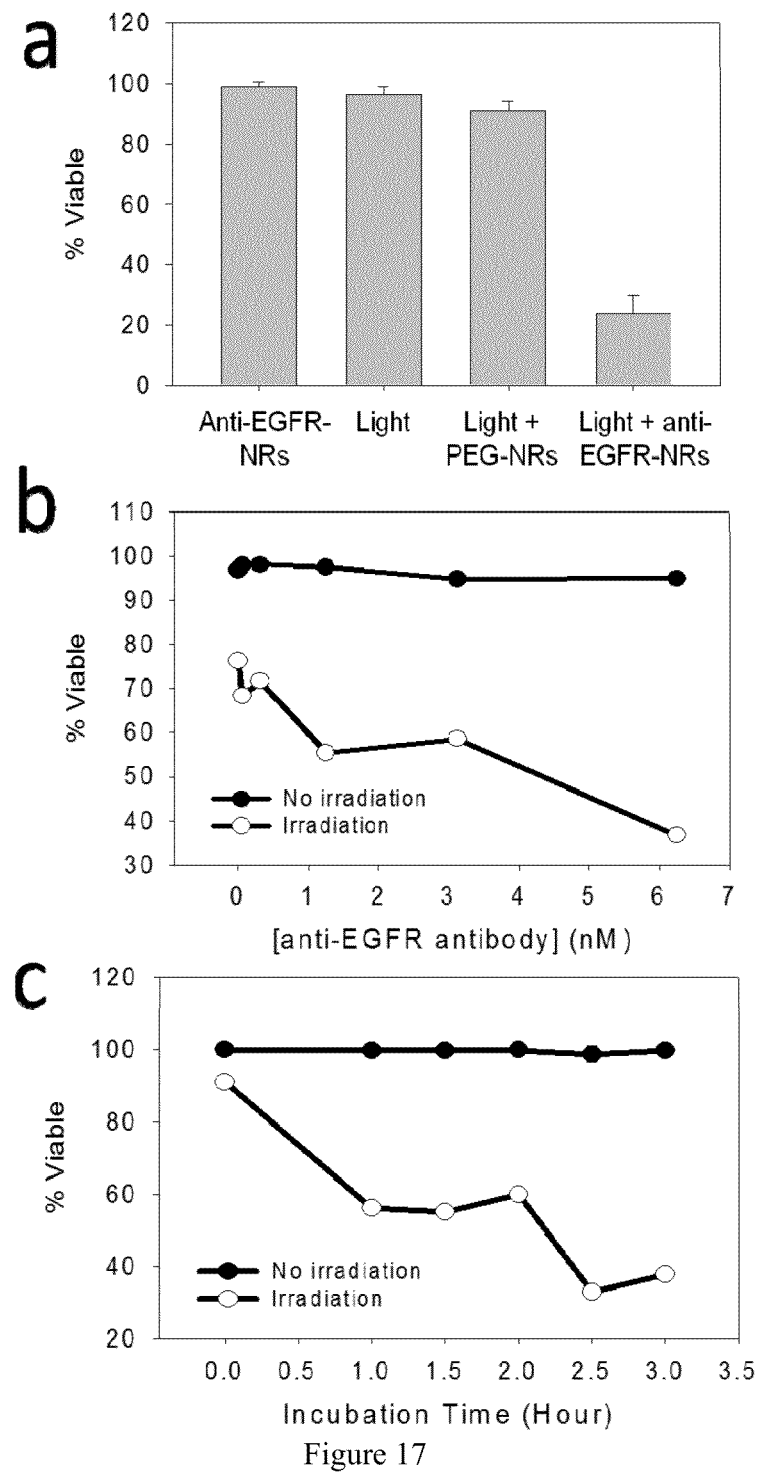

FIG. 17 shows viability data for OSCC15 and MDA-MD231 cells treated with NRs followed by photoirradiation. (a) viability of OSCC15 cells after no treatment (control), irradiation for 5 minutes in the absence of NRs, irradiation for 5 minutes after incubation with PEG NRs ([NR]=9.92 pM), and irradiation for 5 minutes after incubation with anti-EGFR-PD-NRs ([antibody]=4.0 nM; [NR]=9.92 pM); (b) dependence of MDA-MB231 cell viability on anti-EGFR-PD-NR concentration after incubation with anti-EGFR-PD-NRs for 1 hour followed by 5 minutes of irradiation; (c) dependence of MDA-MB231 cell viability on incubation time with anti-EGFR-PD-NRs ([NR]=3.0 pM). Viability was measured (a) 30 minutes or (b,c) 19 hours after a 5 minute irradiation treatment.

Figure 18:
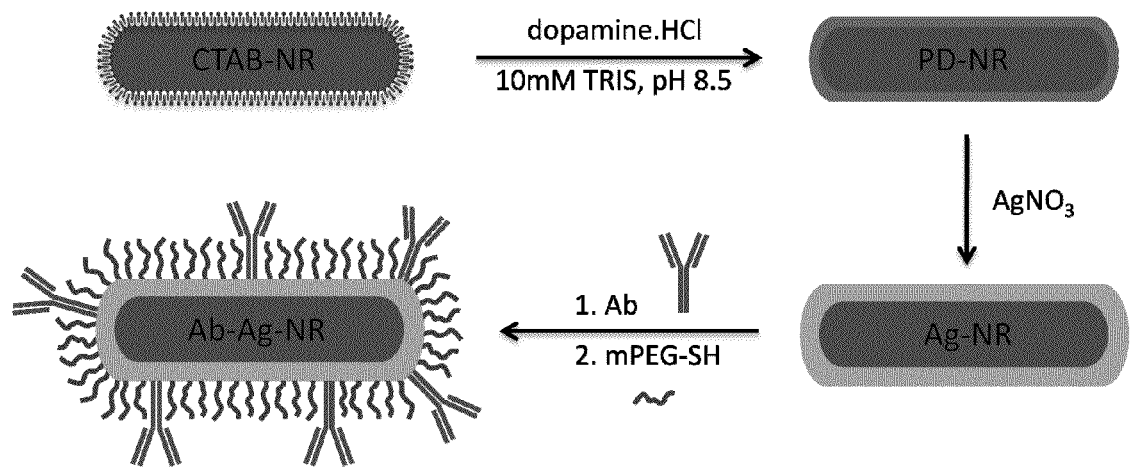

FIG. 18 is a schematic diagram representing the polydopamine-based strategy to form multifunctional antibacterial metal nanorods.

Figure 19:
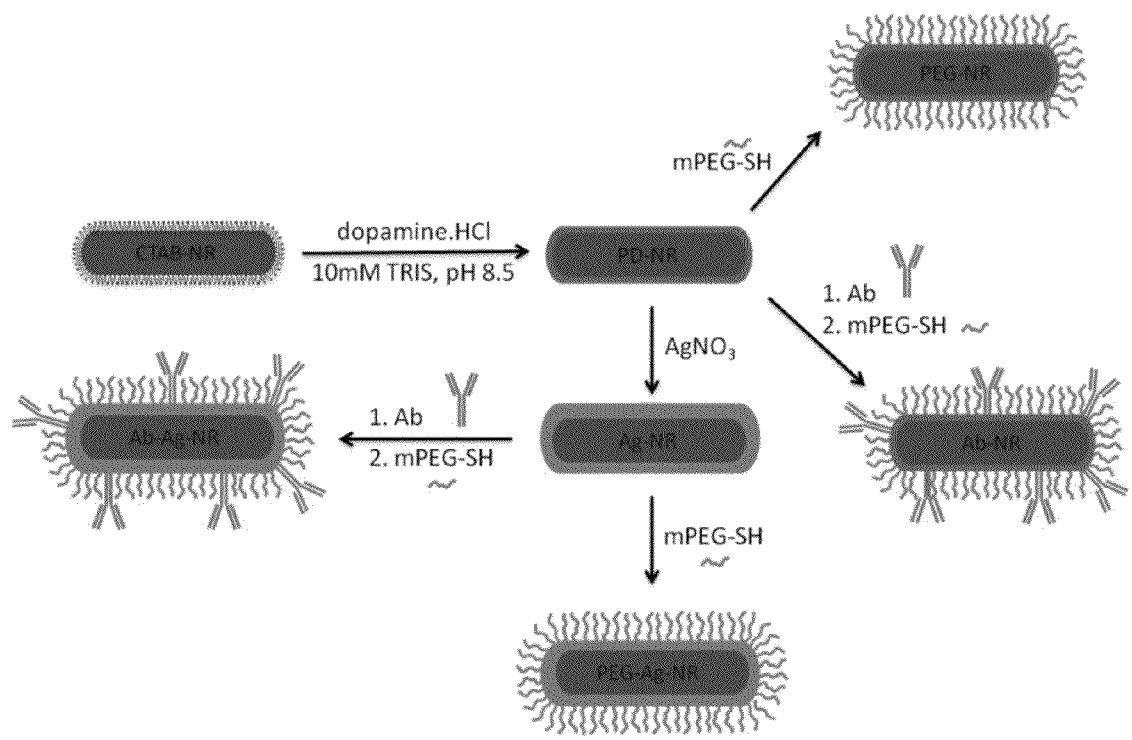

FIG. 19 is a schematic diagram representing the formation of the nanorod formulations described and used in this study.

Figure 20:
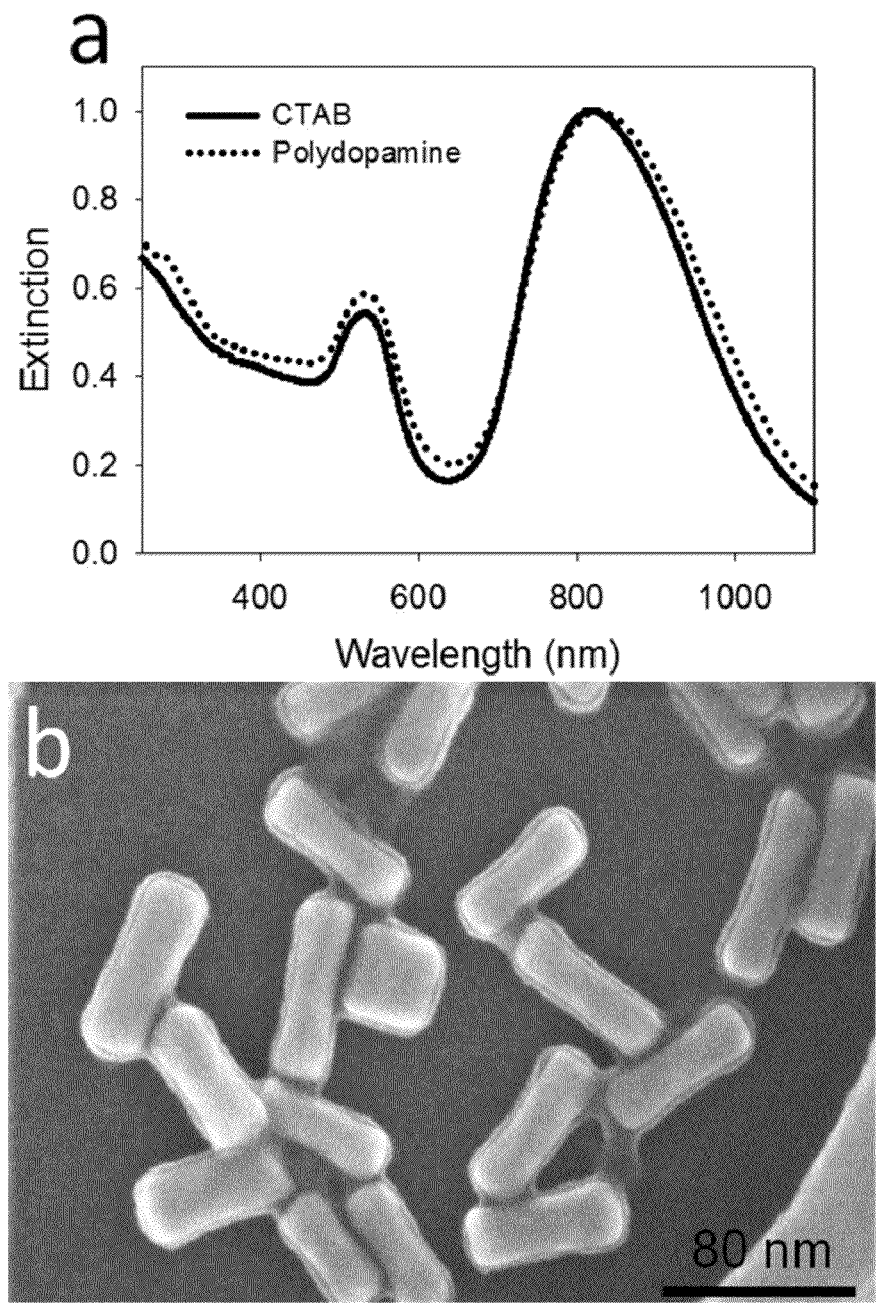

FIG. 20 shows polydopamine (PD) polymerization onto gold NR. (a) Red-shift in the longitudinal surface plasmon resonance of the gold NRs during reaction in 520 µM dopamine in pH 8.5; (b) Secondary electron microscopy of PD-coated NRs (scale bar=80 nm).

Figure 21:
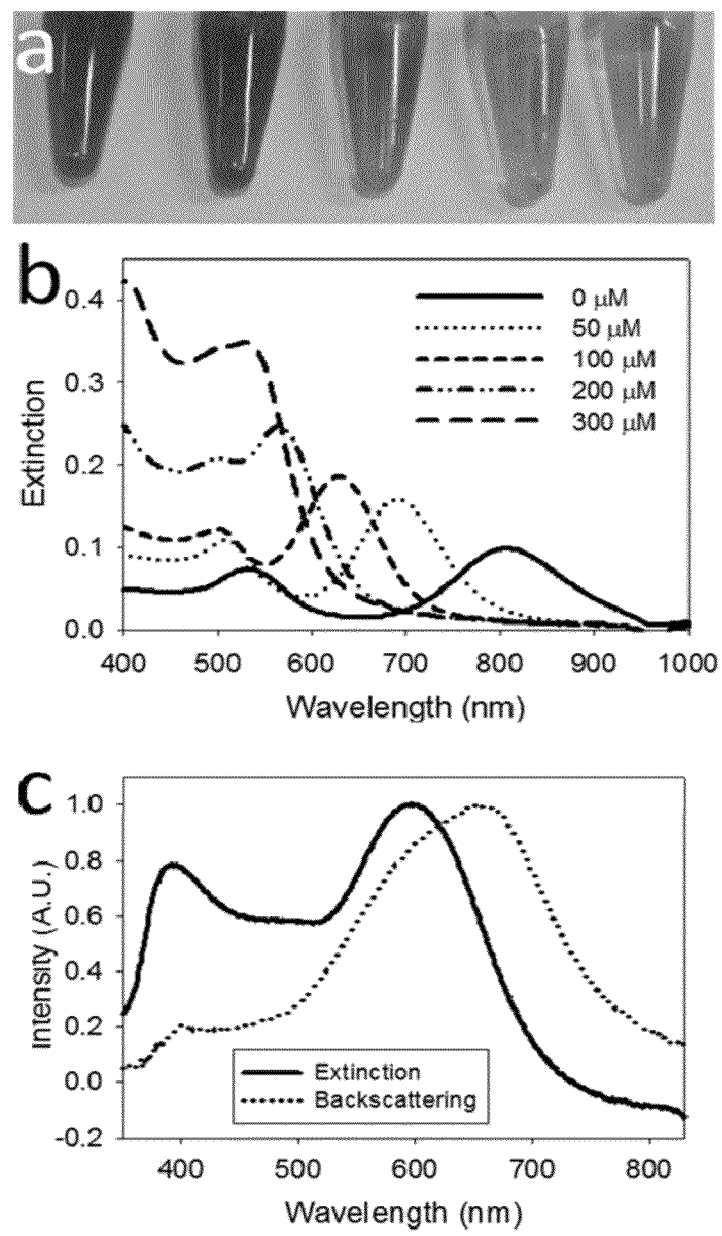

FIG. 21 shows the optical properties of polydopamine-coated gold NRs (PD-NRs) upon silver addition. (a) photos of PD-NR suspensions after addition of (from right to left) 0 µM, 50 µM, 100 µM, 200 µM, 300 µM $AgNO_3$; (b) Optical extinction spectroscopy of PD-NRs after addition of $AgNO_3$, and (c) Optical extinction and backscattering from an individual NR sample after addition of silver.

Figure 22:
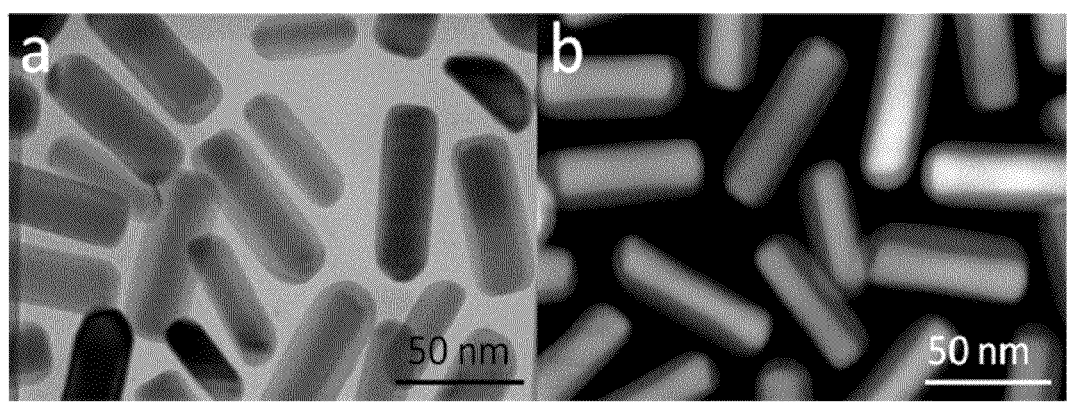

FIG. 22 shows (a) transmission electron microscopy (TEM) image, and (b) Z-contrast electron microscopy (ZCEM) image of poydopamine-coated gold nanorods with silver deposition (PEG-Ag—NRs).

Figure 23:
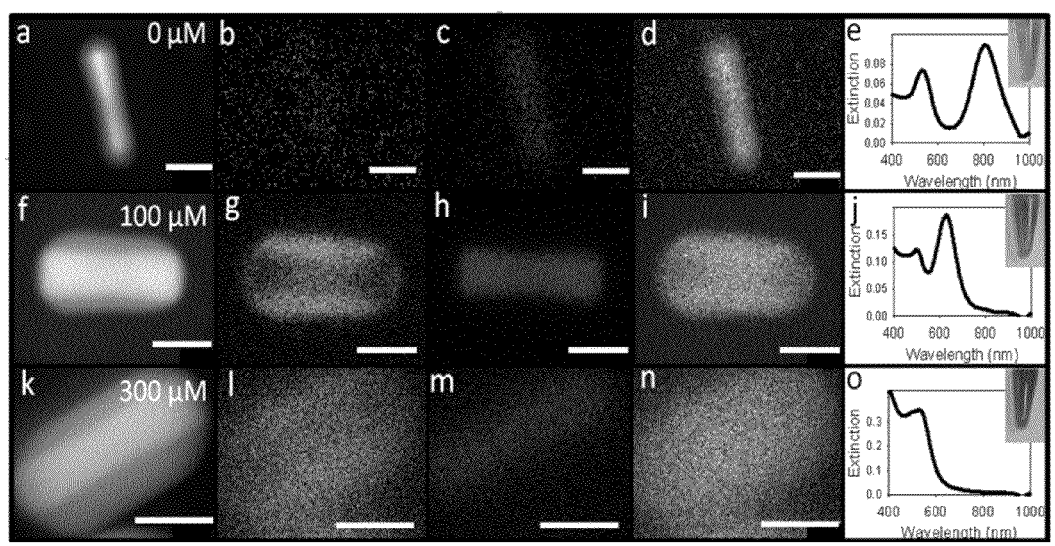

FIG. 23 shows energy dispersive x-ray spectroscopy (EDS) spectral imaging of polydopamine coated NRs (PD-NRs) after addition of 0 µM (top), 100 µM (middle), and 300 µM (bottom) $AgNO_3$: (a, f, k) Z-contrast electron microscopy (ZCEM) image; (b, g, l) silver EDS image; (c, h, m) gold EDS image; (d, i, n) merged image; (e, j, o) optical extinction from respective NR suspensions with color photo of suspensions (inset). Scale bar=20 nm.

Figure 24:
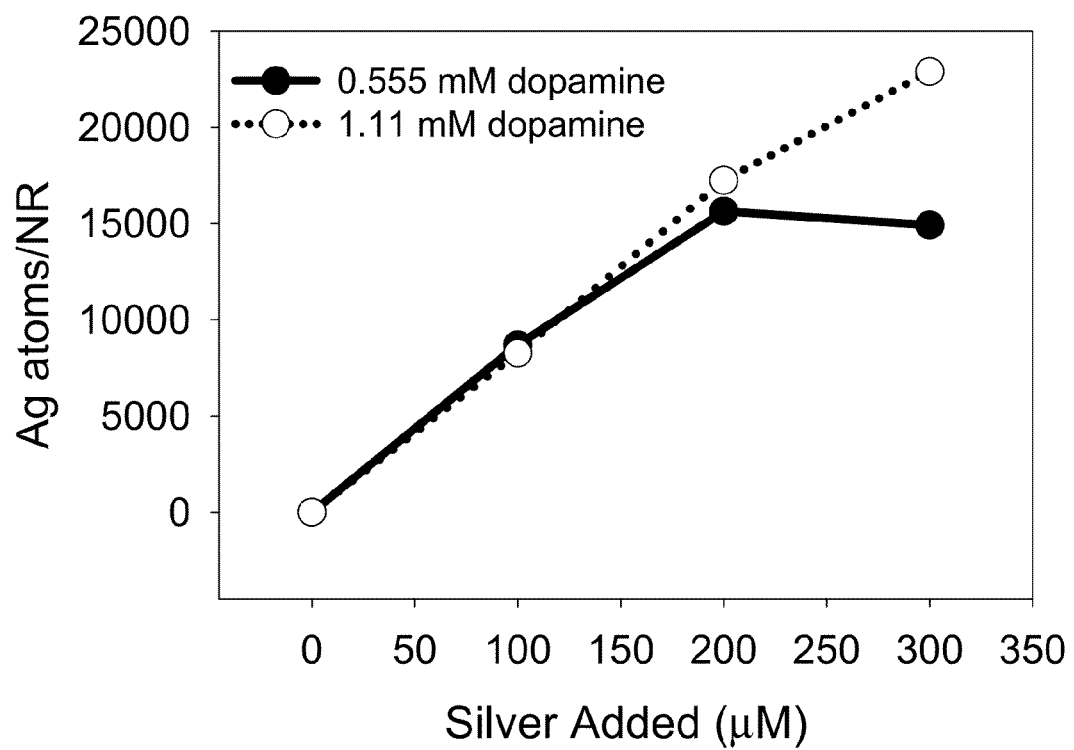

FIG. 24 shows quantification of silver atoms per gold nanorod with inductively-coupled plasma optical emission spectroscopy (ICP-OES).

Figure 25:
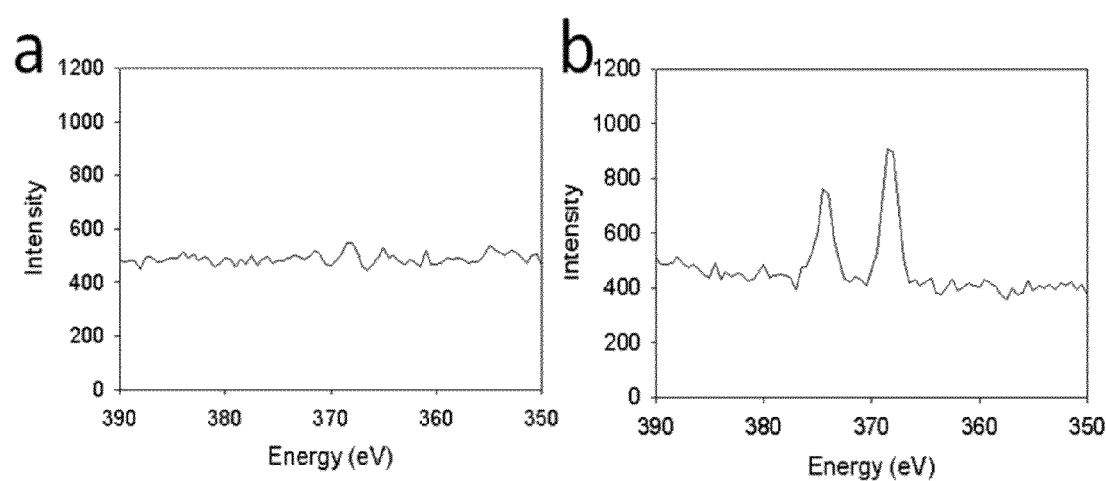

FIG. 25 shows X-ray photoelectron spectroscopy (XPS) of Ag 3d peaks from polydopamine-coated nanorods (PD-NRs) after addition of (a) 0 µM, (b) 160 µM $AgNO_3$.

Figure 26:
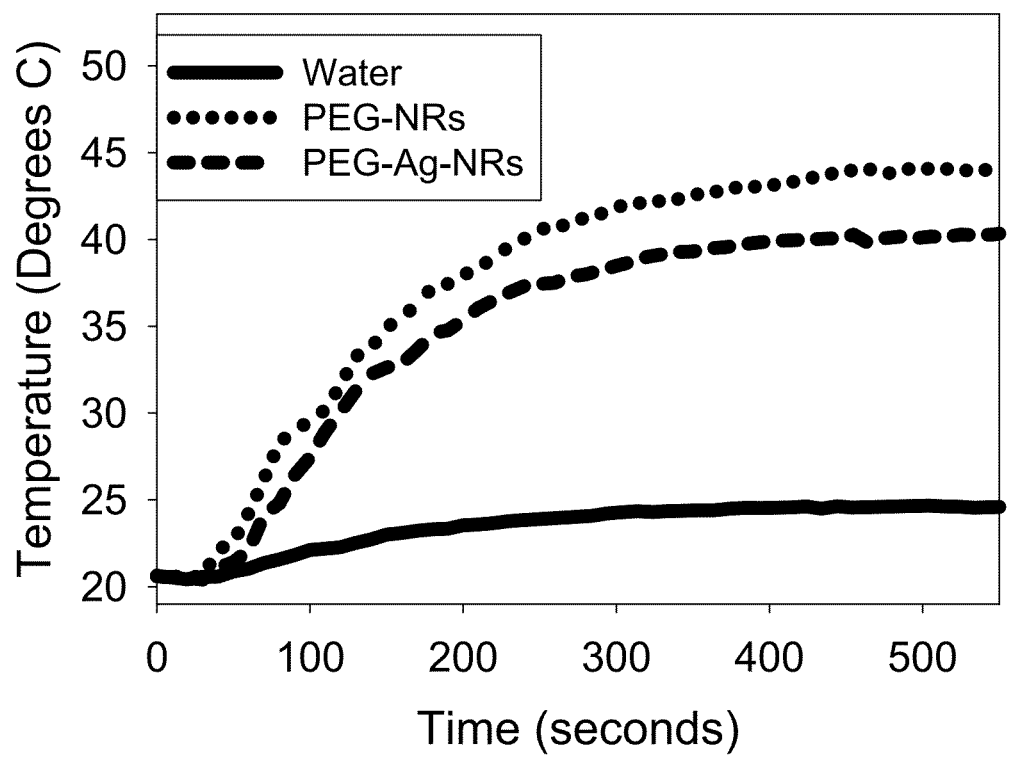

FIG. 26 shows heating profiles of NR suspensions upon irradiation with light.

Figure 27:
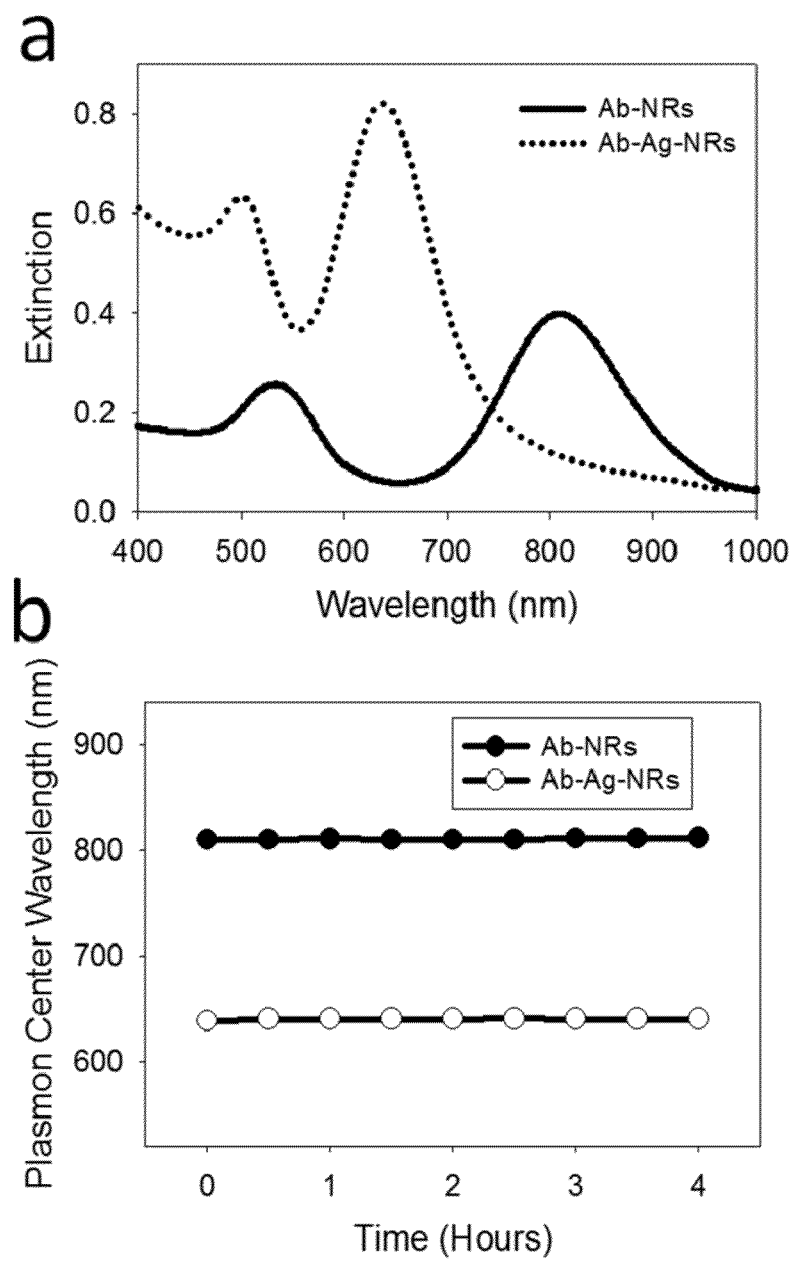

FIG. 27 shows antibody-functionalized metal nanorod (NR) stability in 0.85% salt. (a) Optical extinction spectra of antibody functionalized NRs (Ab-NRs and Ab-Ag—NRs), and (b) shift in the center wavelength of the longitudinal surface plasmon resonance of NRs in 0.85% over time.

Figure 28:
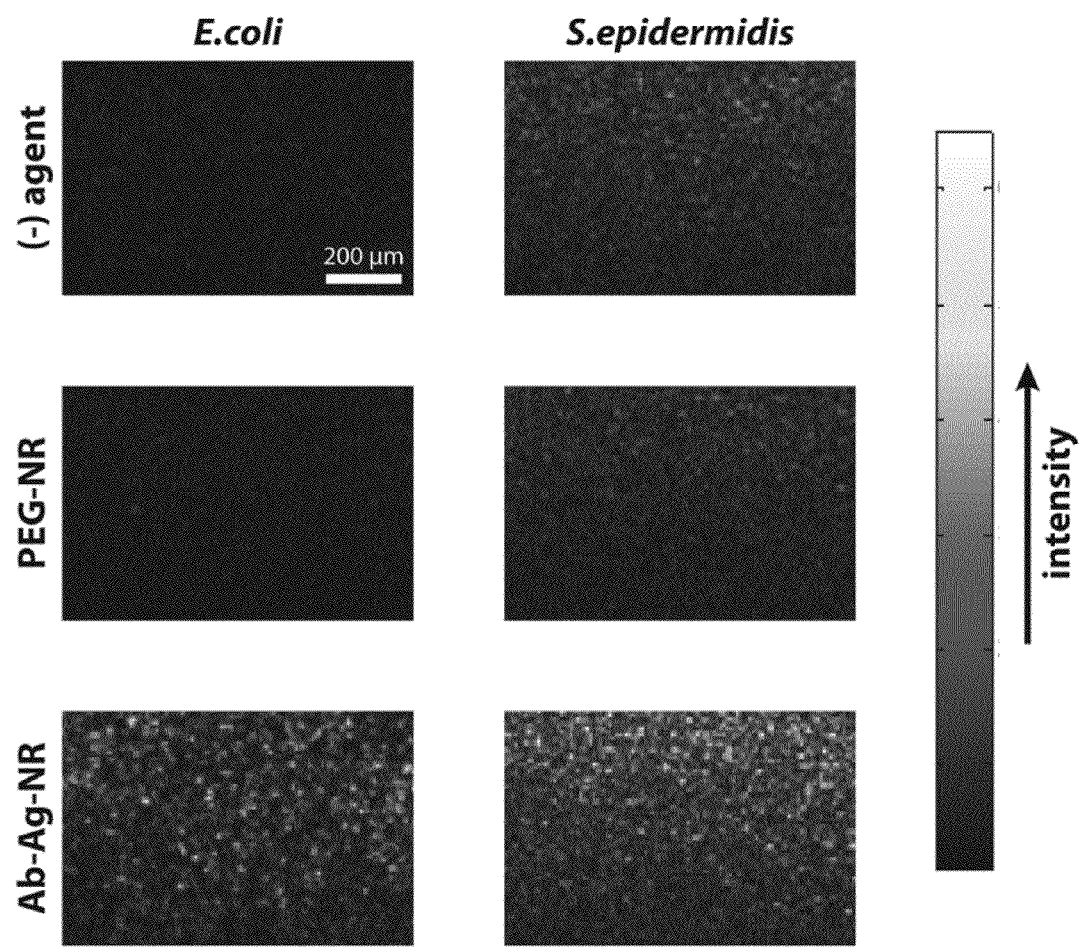

FIG. 28 shows optical coherence tomography (OCT) images of *E. coli* (left) and *S. epidermidis* (right). Images of cell pellets alone (top), pellets incubated with PEG-functionalized nanorods (PEG-NRs, middle), and pellets incubated with NRs functionalized with silver and antibodies (Ab-Ag—NRs, bottom).

Figure 29:
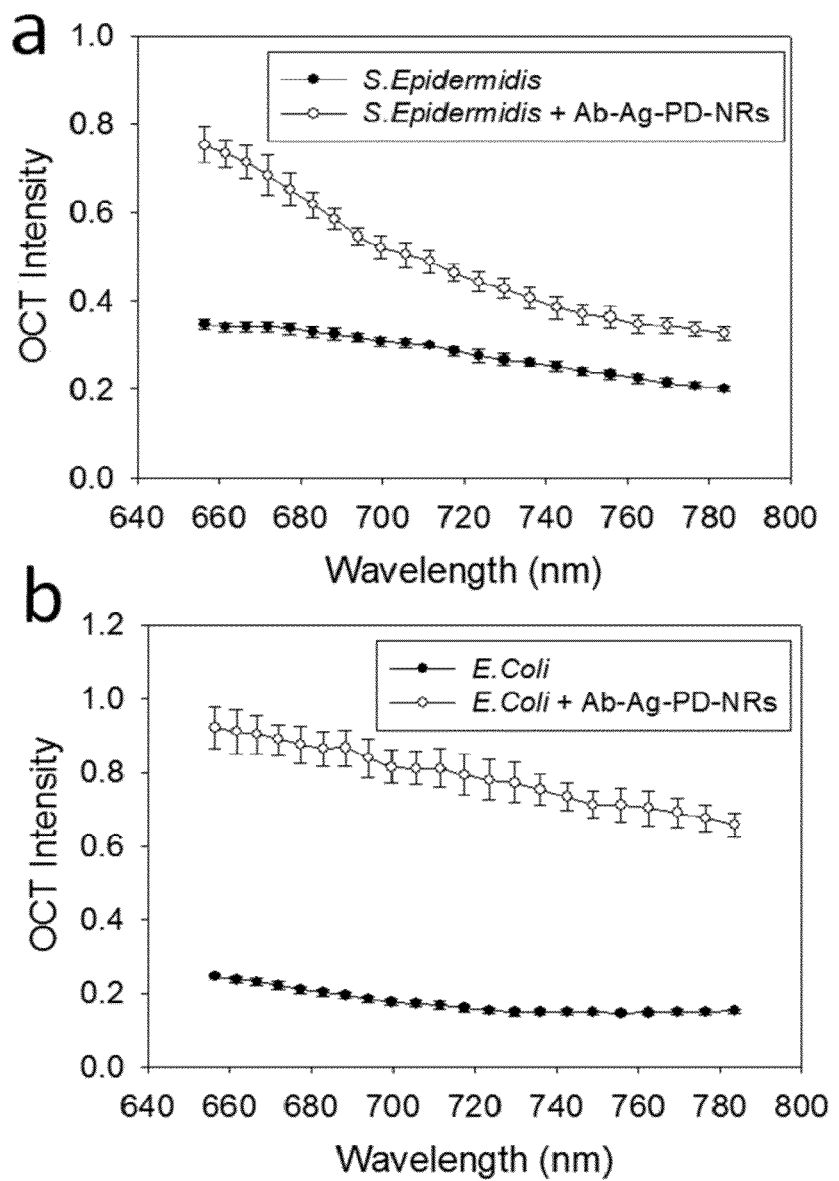

FIG. 29 shows optical coherence tomography (OCT) spectra from images of (a) *S. epidermidis* and (b) *E. coli* seen in FIG. 28.

Figure 30:
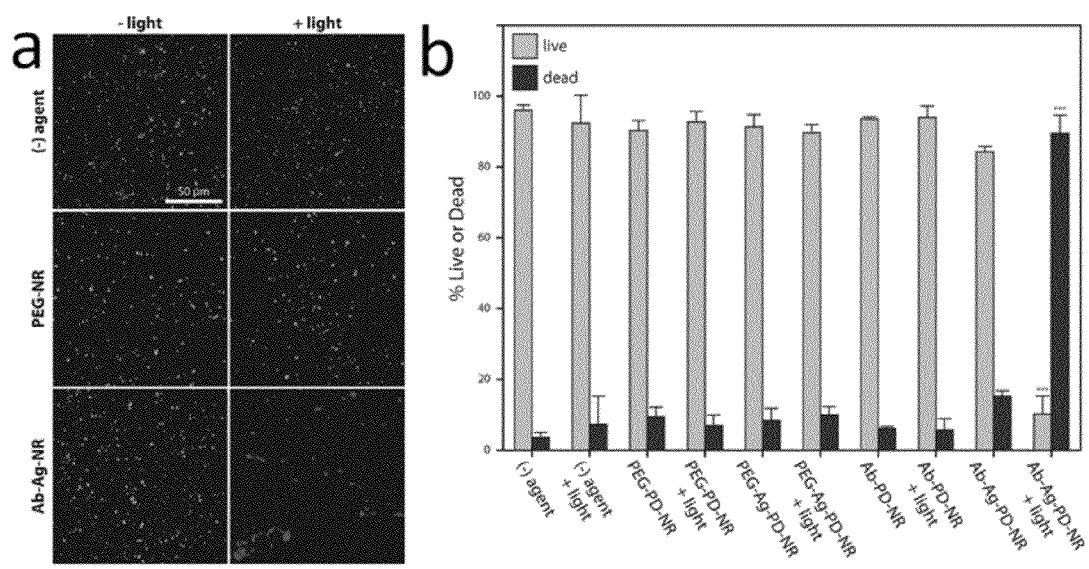

FIG. 30 shows *S. Epidermidis* toxicity after incubation with nanorods (NRs) and irradiation with light. (a) Fluorescent live/dead images and (b) quantitative viability determined from fluorescent images.

Figure 31:
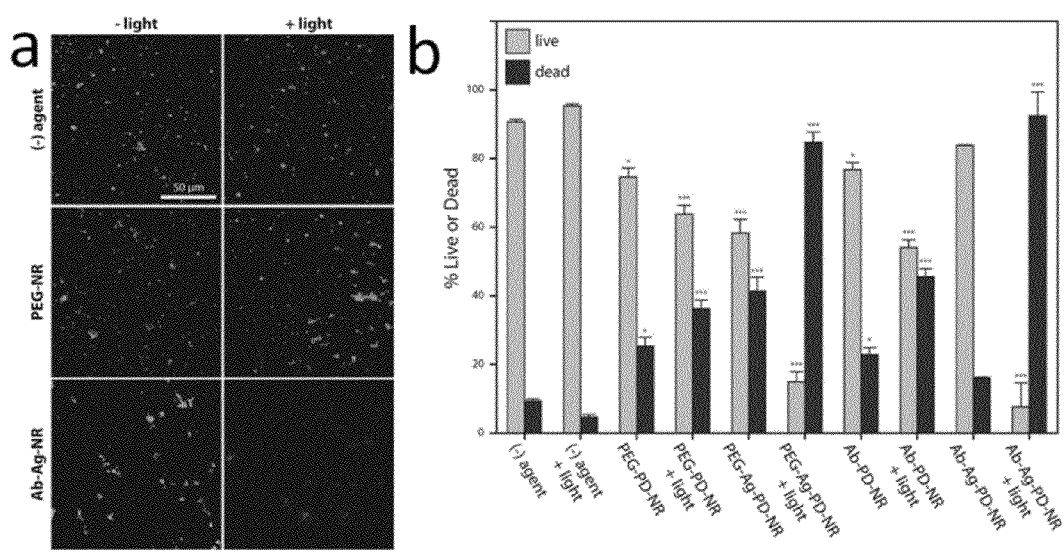

FIG. 31 shows *E. Coli* toxicity after incubation with nanorods (NRs) and irradiation with light. (a) Fluorescent live/dead images and (b) quantitative viability determined from fluorescent images.

Figure 32:
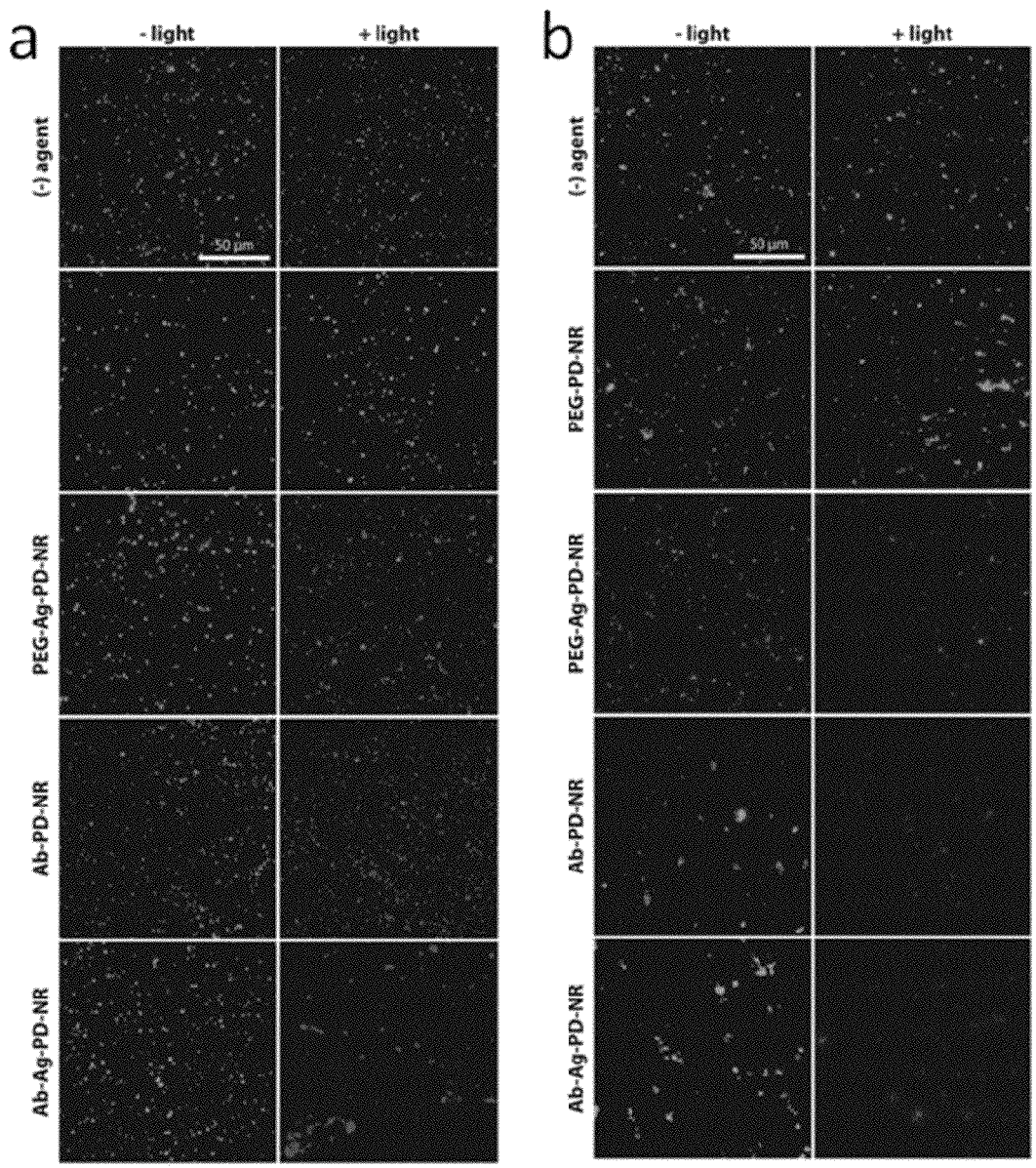

FIG. 32 shows fluorescence images of (a) *S. epidermidis* and (b) *E. coli* treated with nanorods and light and stained with SYTO® 9 green fluorescent nucleic acid stain and propidium iodide.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms and abbreviations used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Polydopamine (PD) has the ability to coat materials using mussel mimetic mechanisms, making it a versatile aqueous adhesive. The inventors report herein the successful coating of metal nanoparticles, specifically gold nanorods, with polydopamine, by contacting the nanorods with an alkaline solution containing dopamine. With the ability to coordinate to metals, π-stack, hydrogen bond, and covalently react through catechols, and to interact electrostatically and react through amines, the polydopamine coating provides a chemical repertoire to form evolutionary modulatory metal nanoparticles.

The resulting multifunctional, multicomponent nanoparticles can be used for multimodal optical or magnetic imaging, such as in bright field microscopy, optical coherence tomography, 2-photon confocal microscopy, or for other targeted diagnostic imaging. The nanoparticles may also be used for photothermal therapy or for cancer, antimicrobial, or other drug delivery.

As outlined in more detail in the examples below, a conformal 'primer' layer of polydopamine was first deposited onto surface plasmon resonant gold nanorods to form a versatile interface for biofunctionalization. In certain embodiments, polyethylene glycol (PEG) polymers were covalently reacted to the biomimetic polydopamine layer to passivate the surface. In certain embodiments, antibodies were immobilized onto the polydopamine-coated nanorods to provide bioactivity, and the number of antibodies per nanoparticle was tuned to be between 8 and 400.

In certain embodiments where anti-cancer nanoparticles were formed, anti-EGFR antibodies were immobilized onto the polydopamine-coated nanorod surface, and the functionalized nanoparticles were found to be stable in serum-containing medium for 24 hours. In some such embodiments, the antibody-functionalized nanorods bound specifically to EGFR-overexpressing oral and breast cancer cells, which were detected in both bright field microscopy and optical coherence tomography. In certain embodiments, targeted nanorods provided a strong synergistic therapeutic response with broad band light irradiation, causing significant death to EGFR-expressing cancer cells in vitro.

In certain embodiments where anti-bacterial nanoparticles were formed, anti-bacterial surface antibodies were immobilized onto the polydopamine-coated nanorod surface. In some such embodiments, silver was incorporated into the polydopamine coated nanorod surface. The antibody-functionalized nanorods bound specifically to bacterial cells, and targeted nanorods provided a strong synergistic therapeutic response with broad band light irradiation, causing significant death to bacterial cells in vitro. This effect was especially pronounced for nanorods that included silver.

The versatile polydopamine surface modifications demonstrated herein can be applied to functionalize nanoparticles composed of many materials with a broad range of bioactive molecules, such as antibodies, peptides, and DNA aptamers for cancer treatment and other biomedical applications. With emerging advances in biotechnology such as high throughput genetic screening, the polydopamine-coated nanoparticles have the adaptable chemical repertoire to facilitate the synthesis of individualized, multifunctional diagnostic and therapeutic agents for a broad range of diseases. The versatility of catechol chemistry allows the polydopamine surface to be functionalized in a variety of ways, as demonstrated below for multimodal targeted imaging and synergistic therapy of cancer and bacterial infections.

Further, polydopamine itself is a photothermal modulatory material. It has a similar structure to that of melanin, a natural material used for photoprotection by converting light energy into heat energy. Therefore polydopamine coatings with tunable thicknesses on the nanorod allow for control over the conversion of light energy to heat energy for optimization of metal nanoparticles for optical contrast agents and photothermal agents.

Accordingly, the disclosure encompasses nanoparticles that include a metallic core and a polydopamine coating disposed on at least part of the surface of the metallic core. As used herein, the term "nanoparticle" means a particle having a length along any axis passing through the center of the particle of from 1 to 100 nanometers. In some embodiments, the metallic core is a nanorod. As used herein, the term "nanorod" refers to a nanoparticle having a substantially cylindrical shape. In some such embodiments, the metal nanorod has a length of 1-100 nanometers, 10-90 nanometers, 20-80 nanometers, 30-70 nanometers, or 40-60 nanometers, and the metal nanorod has a width (diameter) of 1-50 nanometers, 5-30 nanometers, or 10-20 nanometers. In some embodiments, the metallic core is made of gold.

Dopamine is a bifunctional catecholamine having the following chemical structure:

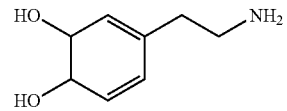 [SMILES: NCCC1=CC(O)C(O)C=C1]

Under conditions typical of a marine environment (e.g., buffered to 8.5), a dilute solution of dopamine can self-polymerize to form polydopamine (H. Lee at al., *Science* 318(5849) (2007): 426-430). The mechanism likely involves oxidation of the catechol to a quinone, followed by polymerization in a manner reminiscent of melanin formation, which occurs through polymerization of structurally similar compounds. See scheme 1 below:

Scheme 1: proposed mechanism for polydopamine formation.

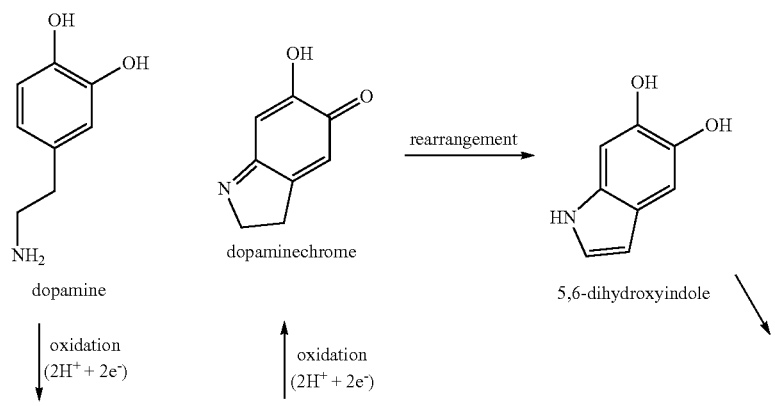

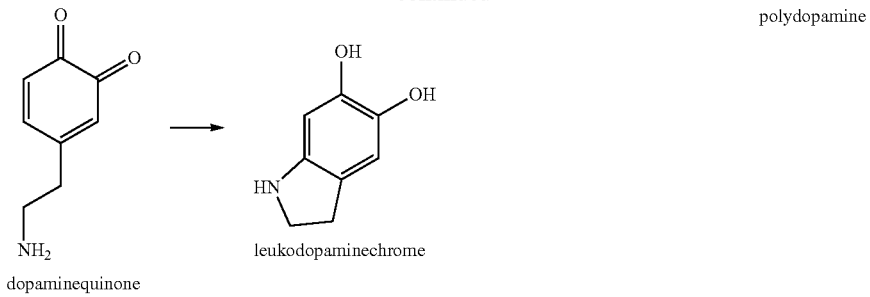

dopaminequinone → leukodopaminechrome → polydopamine

The inventors report herein the self-polymerization of dopamine to form a polydopamine coating onto the surface of metal nanopaparticles, specifically onto the surface of gold nanorods. Once the polydopamine is coated onto the metal surface, it may be modified in a number of ways, depending on the biological, optical, and/electromagnetic properties needed to facilitate the desired function of the nanoparticles.

Metal NPs have SPR material properties that can be harnessed for a variety of biomedical applications when their surfaces are biofunctionalized, including in the photothermal treatment of cancer or bacterial cells. Furthermore, the biomimetic strategy disclosed herein can be expanded to include other functional nanomaterials like superparamagnetic iron oxide, and other targeting and therapeutic moieties such as small molecule drugs and other cell-surface targeting antibodies, in order to form multifunctional agents for specific diagnosis and combination therapy for complex resistant diseases such as heterogeneous cancers and antibiotic resistant bacteria.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Polydopamine-Based Assembly of Multifunctional, Multicomponent, Multimodal Metal Nanoparticles for Synergistic Photothermal Mediated Diagnosis and Therapy In this example, we describe the coating of a polydopamine (PD) layer onto the surface of gold nanorods. We further describe modifications to the polydopamine surface of the nanorods in order to (1) immobilize silver into the surface to tune the surface plasmon resonance and the toxicity of the metal nanoparticles; (2) immobilize magnetic iron oxide nanoparticles into the layer to provide magnetic targetability; (3) react polyethylene glycol molecules into the layer with amine, thiol, catechol, and histidine functionalities to provide stealth characteristics, as well as provide proof of principle for diverse functionalization chemistry mediated by catechol oxidation to quinine; (4) immobilize chitosan onto the gold nanorods to provide additional molecular functionality; (5) react sugar-containing peptoids with catechol and amine containing anchors onto gold nanorods to provide stealth properties; (6) react catechol-containing poly-N-isopropylacrylamide (pNIPAM) onto the gold nanorod surface to provide thermal and photothermal responsive solubility; (7) conjugate anti-EGFR antibodies onto the surface to provide specific EGFR targeting and inhibition; and (8) conjugate pro-apoptotic drugs into the layer to provide pH dependent release of pro-apoptotic drugs.

Polydopamine (PD) was polymerized onto the surface of gold nanorods (NRs) to form a multifunctional, multicomponent anticancer surface. Specifically, silver was deposited into the PD layer to modulate toxicity and tune the SPR throughout the visible and near-infrared portions of the electromagnetic spectrum. PEG was reacted into the PD layer through Michael-type addition and Schiff base reactions to inhibit non-specific interactions and increase solubility in physiological conditions. The proteasome inhibitor bortezomib was coordinated to catechols in the PD layer to provide a pro-apotptic effect, and the anti-EGFR antibody ERBITUX® (cetuximab) was reacted through quinone-mediated cross-linking reactions to provide NPs with specific targeting and growth factor pathway inhibition. NRs were identified on oral cancer cells with bright field microscopy, optical coherence tomography, and 2-photon excited confocal microscopy. Finally, targeted NR-mediated photothermal therapy was performed.

Importantly, the NPs provide multiple mechanisms of treatment, including specific targeting and inhibition of EGF pathways, toxicity from silver, pH-dependent release of bortezomib in acidic cancer microenvironments, and thermal heating to cause necrosis and permeabilize membranes to increase drug uptake. Taken together, these catechol-based metal nanoparticles provide multimodal imaging and synergistic therapy for cancer.

Dopamine hydrochloride, Cetyltrimetylammonium bromide (CTAB, 99%), sodium tetrachloroaurate(III) dihydrate (NaAuCl$_4$.2H$_2$O, 99%), sodium borohydride (NaBH$_4$, 98%), ascorbic acid, glycine, silver nitrate (AgNO$_3$, 99%), and phosphotungstic acid (10% solution) were obtained from Sigma-Aldrich (St. Louis, Mo.). The pH value of the solution glycine solution (0.2M) was adjusted with 2M sodium hydroxide to 8.0. PEG-SH (MW=5000) was purchased from Laysan Bio (Arab, Ala.). ERBITUX® (cetuximab) infusion was acquired from the Northwestern pharmacy (Chicago, Ill.). Ultrapure, deionized water (18.2 MΩ·cm) was used to prepare all of the aqueous solutions.

Synthesis of Gold Nanorods (NRs).

The synthesis of Au—Ag NRs was performed according to a slightly modified method previously described in the literature. Briefly, cetyltrimethylammonium bromide (CTAB) aqueous solution (0.2 M, 5.0 mL, heated to 30° C.) was mixed with 0.5 mM of NaAuCl$_4$ (5.0 mL). Ice-cold 0.01 M NaBH$_4$ (0.6 mL) was added to this solution and sonicated for 5 minutes to form a brownish-yellow seed solution. Then 50.0 mL of 0.2 M CTAB were gently mixed with 50.0 mL of 1.0 mM NaAuCl$_4$ and 0.1 mL of 0.1 M of silver nitrate to form a growth solution. Ascorbic acid was added to the solution as a mild reagent (78.8 mM, 0.7 mL), followed by addition of 120 μL of the seed solution. After 45 minutes, this Au NR seed solution was used directly to prepare the Au—Ag NRs. Simply, 100 mL of seed solution was mixed with 100 mL of 0.2 M glycine (pH 8.0). This solution was allowed to react overnight without stirring at ambient temperature.

PD Polymerization onto Gold NRs.

1 mL of gold NR suspension was centrifuged and resuspended in 1.7 mL of 10 mM TRIS or bicine buffer (pH 8.5). NRs were reacted in 258 μM-10.2 mM dopamine under sonication for 30 minutes-18 hours. 32-320 μM $AgNO_3$ was added under stirring to incorporate silver into the PD-layer. To pegylate the NRs, 0.2-3 mM mPEG-SH, mPEG-$NH_2$, mPEG-NH—Ac, and mPEG-H, and mPEG-C were added to solutions either simultaneously with or 30 minutes-1 hour after dopamine addition. Bifunctional PEGs were also incorporated into the layers with the addition of biotin-PEG-dopamine polymers. Similar experiments were performed with peptoid molecules containing DOPA-Lys anchor, poly N-isopropylacrylamide polymers containing catechol functionalities, and chitosan. Samples were sonicated for 2 additional hrs, rocked overnight, and UV-Vis-NIR spectrum was acquired. Samples were centrifuged at 9000 rpm for 15 minutes; supernatant solution was removed. Pelleted NRs were resuspended in 2 mL of ultrapure water, and another UV-Vis-NIR spectrum was acquired. To perform experiments in salt, pelleted pegylated NRs were resuspended in 100 mM sodium chloride, and monitored with optical spectroscopy for 3 days.

Iron Oxide Nanoparticle Synthesis.

99.5 mg $FeCl_2*4H_2O$ and 270.3 mg $FeCl_3*6H_2O$ was dissolved in 30 mL water and 605 μL 6N NaOH under slow stirring and reacted under Ar for 1.5 hours. Particles were pelleted by magnet, supernatant was removed, and pellet was resuspended in ultrapure water.

Iron Oxide Nanoparticle Conjugation to Gold NR.

1 mL of gold NR suspension was centrifuged and resuspended in 1.7 mL of 10 mM TRIS or bicine buffer (pH 8.5). NRs were reacted in 258 μM dopamine under sonication for 30 minutes and then centrifuged. The supernatant was discarded, the NRs were resuspended in 2 mL ultrapure water, and 25 μL 2 mM stock iron oxide solution was added. The mixture was sonicated for 2 hours, the conjugates were pelleted magnetically, and the clear supernatant was removed. A TEM grid was prepared, the pellet was resuspended in 1 mL ultrapure water, and UV-Vis spectra were acquired.

Antibody Immobilization on Gold NRs.

1 mL of metal NR suspension was centrifuged at 9000 rpm and 23° C. for 10 minutes, supernatant was removed, and the pellet was resuspended in 1.7 mL of 10 mM TRIS buffer (pH 8.5). NRs were reacted in 516 μM dopamine under sonication for 30 minutes. To silverize the layer, 6.5-65.5 μL of 10 mM $AgNO_3$ was added under stirring. 100 μL of 2 mg/mL ERBITUX® (cetuximab) infusion added to the solution and sonicated for 30 minutes. Samples were further centrifuged, supernatant was removed, pellets were resuspended in ultrapure water, and UV-Vis-near infrared (NIR) spectrum was acquired. To further confirm conjugation of antibodies to gold NRs, 10-504 solution of antibodies labeled with 10 nm gold NRs were incubated with PD-coated gold NRs, centrifuged, and imaged with electron microscopy.

Bortezomib Immobilization onto Gold NRs.

1 mL of metal NR suspension was centrifuged at 9000 rpm and 23° C. for 10 minutes, supernatant was removed, and the pellet was resuspended in 1.7 mL of 10 mM TRIS buffer (pH 8.5). NRs were reacted in 516 μM dopamine under sonication for 30 minutes. 1.2 mg bortezomib was dissolved in 300 μL DMSO and added to the NR suspension which was sonicated for 30 minutes. 220 μM PEG-SH was added to the suspension under sonication for 30 minutes, and then suspensions were centrifuged and washed twice to remove excess dopamine and unbound bortezomib. To conjugate ERBITUX® (cetuximab) and bortezomib to NRs, the same protocol was followed, with PEG-SH replaced by 100 μL 2 mg/mL ERBITUX® (cetuximab) infusion.

Optical Spectroscopy.

A Hitachi (Hitachi City, Japan) U-2010 Spectrophotometer was used to acquire optical spectra in a two-beam geometry of samples. 10 mM TRIS buffer (pH 8.5) was used for the reference beam. Spectral scans were performed over the 200-1000 nm range of wavelengths in the UV-Visible-NIR region of the spectrum. A deuterium lamp was used for the 200-340 nm UV range illumination and a halogen lamp was used for the visible and NIR illumination. Spectral resolution was 1 nm.

Electron Microscopy (EM).

Pelleted NRs (5 μL) were dropped on EM grids (Ted Pella, Redding, Calif.) and allowed to dry. To stain PEG, grids were immersed in 10% phosphotungstic acid solution for 90 seconds three times, and then immersed in pure water for 30 seconds. Transmission EM (TEM), Z-contrast EM, secondary EM (SEM), and energy dispersive X-ray spectroscopy (EDS) spectral imaging were performed on a Hitachi HD-2300 Ultra High Resolution FE-STEM (Hitachi City, Japan).

Multimodal Cellular Imaging.

Oral squamous cell carcinoma 15 (OSCC15) cells were grown in DMEM containing 10% FBS and 4% gentamycin. To image cells with NRs, 2 mL of trypsin was added to confluent plates of OSCC15 cells, cells were removed, and 400 μL was added to 2 mL of DMEM high glucose media. Cells were centrifuged at 1500 rpm for 5 minutes, supernatant was removed, and 2 mL more media was added. NR suspensions from above were added to the cells and incubated for 30 minutes. Cells were centrifuged at 1500 rpm for 5 minutes, supernatant was removed, 2 mL of media was added, and finally cells were centrifuged and plated onto glass optical microscopy slides.

Bright field images were acquired in a Leica DMRX microscope. Additionally, optical coherence tomography (OCT) was acquired. A visible band Fourier-domain OCT was used in this study. The system adopts a commonpath parallel configuration and the schematic is described in a previous paper. The parallel configuration allowed simultaneous 2D B-scan OCT image acquisition (~1 mm cross and ~300 μm deep) with 5 fps frame rate. 3-D images were obtained by scanning the sample stage across the B-scan image plane. The axial resolution was ~1.5 μm given by the bandwidth (540-650 nm), and the transverse resolution and depth of focus were ~6 μm and ~200 μm, respectively. 2-photon confocal microscopy was performed with a 40× oil immersion objective in an Inverted Zeiss Axio Observer.Z1 Confocal Microscope. Differential interference contrast (DIC) images and 2-photon excited images were acquired in two channels. A spectrum of the 2-photon emission between 400 nm and 650 nm with 10 nm resolution was acquired in an Upright Zeiss LSM 510 Confocal Microscope using the same Mai:Tai laser described above.

Photothermal Studies.

In addition, NRs were embedded in an alginate gel and imaged under a range of powers. Finally, suspensions of CTAB-coated and PD-coated NRs were irradiated with varying incident powers, and the 2-photon excited visible emission intensity was quantified.

Cellular Toxicity Experiments.

For long term toxicity experiments, NRs (0-95 μM Au) were incubated with OSCC cells in 6 and 12 well plates with 1 mL DMEM high glucose media for 20-48 hours. 15 minutes before toxicity quantification, 1 μL 4 mM calcein and 1 μL 4 mM ethedium bromide was added to each well, and cells were incubated for 15 minutes. Fluorescence microscopy was performed on a Leica DM IRB light microscope and a QImaging QI Click camera. Red- and green-channel were acquired for each condition in triplicate, cells were counted manually, and an average percent viable cell percentage was calculated for each condition.

NP-Mediated Photothermal Therapy.

OSCC15 cells were cultured in 6-well plates. Cells were incubated with ERBITUX® (cetuximab) conjugated NRs (62.5 μM Au) for 1 hour, and then each well was irradiated with 50 mW NKT photonics SUPERK™ Versa laser source for 5, 10, or 15 minutes. Spot size was 1 mm.

Magnetic Targeting and Photothermal Irradiation Experiments.

In the magnetic targeting experiments, 0-14 pM NR were added to 12 well plates of MDA-MB-231 or MCF7 cells. A magnet was placed underneath the wells for 30 seconds, and then the cells were irradiated with the 50 mW VersaK source described in chapter 3 and 4. To quantify toxicity, 1 μL of 2 mM calcein and ethedium homodimer were added to each well and incubated for 15 minutes. Fluorescence microscopy was performed on a Leica DMIRB microscope, with a 250 W maximum Hg arclamp, and a QImaging QIClick detector. Calcein-stained and ethedium-homodimer stained cells were counted, and % cell viability was quantified. Triplicate images were acquired for each condition.

Results.

Figure 1:
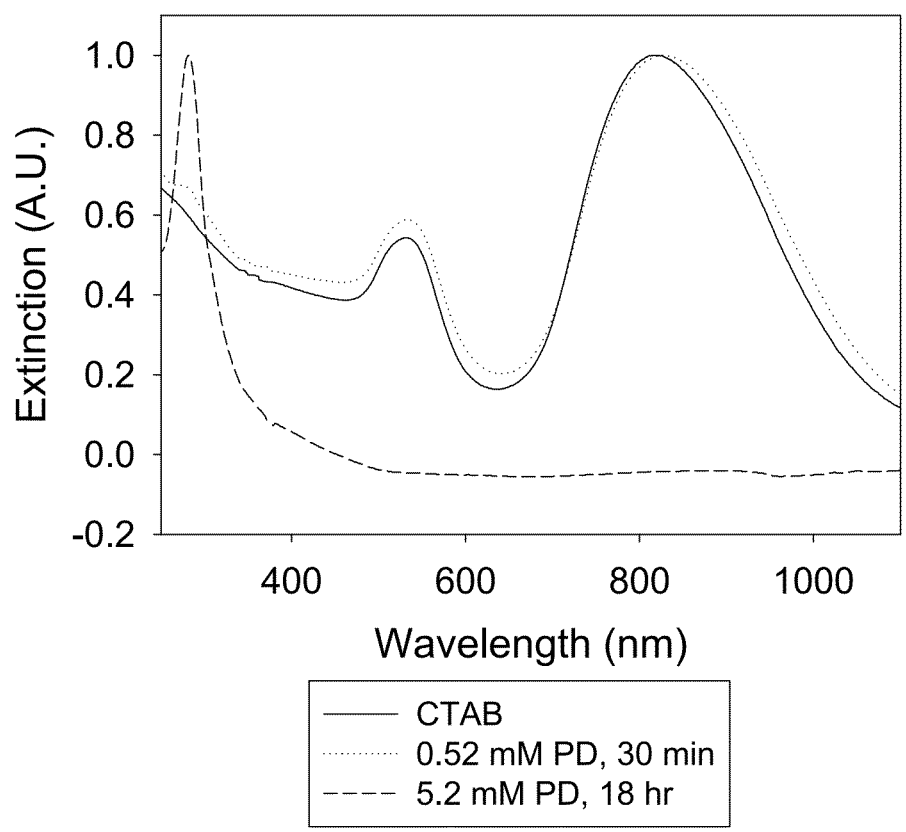
FIG. 1 is a graph showing UV-Vis extinction for three different nanorod suspensions.

Suspensions of CTAB-stabilized gold NRs were synthesized with a previously reported protocol. Once formed, the apexes of the transverse and more intense longitudinal extinction peaks of CTAB-gold NRs were located between 515-530 nm and 756-872 nm, respectively, and were stable over the span of 6-12 months. Suspensions were imaged under TEM and had an average length of 50±8 nm and width of 15±3 nm. To exchange the CTAB coating with a more functional PD layer, gold NR suspensions were incubated in dopamine solution at pH 8.5. When NRs were mixed in 5.2 mM dopamine solutions and allowed to react overnight, brown to black aggregates formed on the polystyrene tubes and in suspension, and the plasmon peaks from the NRs were permanently lost in the remaining liquid sample (FIG. 1). When NRs were mixed in 520 μM dopamine solutions and allowed to react overnight, a stable darkened suspension formed.

Silver was immobilized into the PD layer surrounding the NR. $AgNO_3$ (0 to 320 μM) was added to the polymerizing suspension 30 minutes after addition of 516 μM dopamine. Suspension color changes occurred within 1 minute of silver addition, which included red (no silver), orange (32 μM), yellow (96 μM), green (160 μM), and blue (320 μM). Electron microscopy was performed on PD-coated NRs with and without the addition of silver nitrate. A homogeneous distribution of pure gold NRs (>95%) was evident in samples with no additional silver added. Under both TE mode and Z-contrast imaging, core-shell NRs were present in samples where dopamine and silver were both added.

Figure 2:
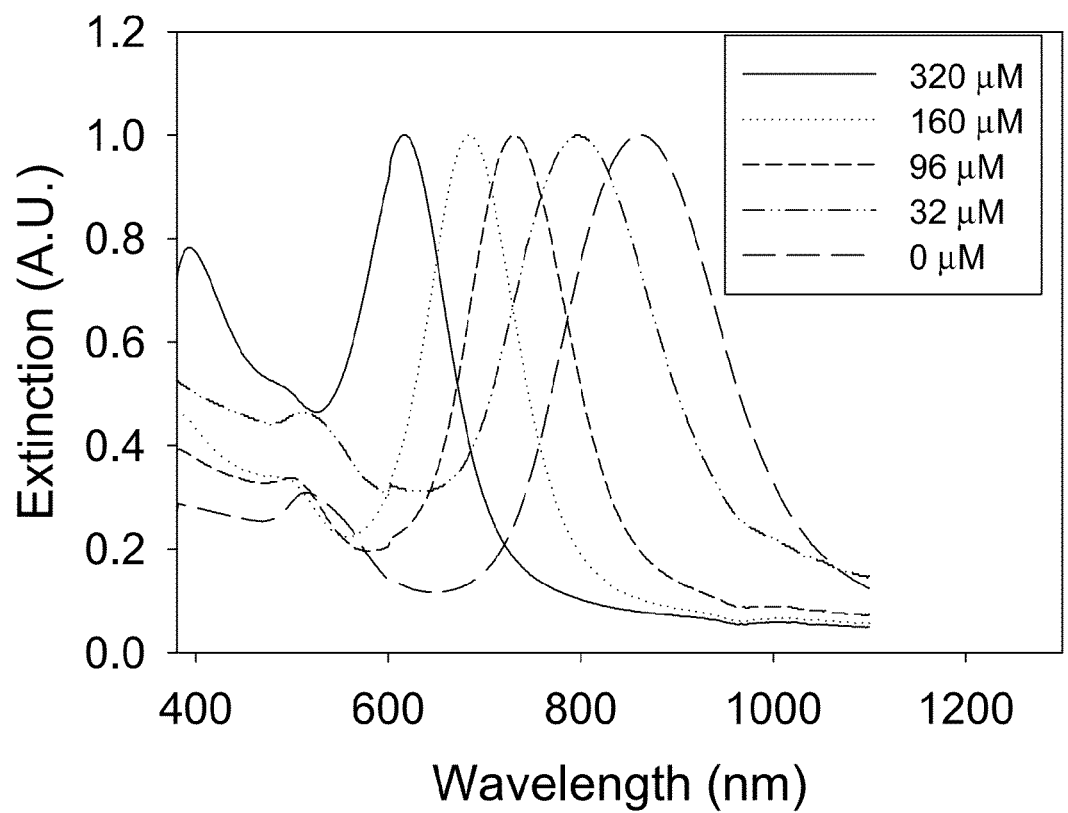
FIG. 2 is a graph showing the results of optical extinction spectroscopy of polydopamine (PD)-coated gold NRs after the addition of silver.

Coatings of tunable thickness ranging from 2.3 nm (32 μM) to 7.0 nm (320 μM) were correlated with the color change. EDS spectral imaging confirmed the presence of the silver coating around a gold NR. The longitudinal SPR peak of the NR sharpened and blue-shifted from 864 nm into the visible when coated with silver (FIG. 2). With a 7 nm thick coating, the SPR shifted to 617 nm, with a 3.3 fold increase in the plasmon extinction intensity per particle. The SPR band width decreased from 194 nm with no silver to a minimum of 118 nm with 164 μM silver. Only a very slight blue shift of 10 nm with no significant change in the line width occurred with the addition of silver in a control sample without dopamine.

Figure 3:
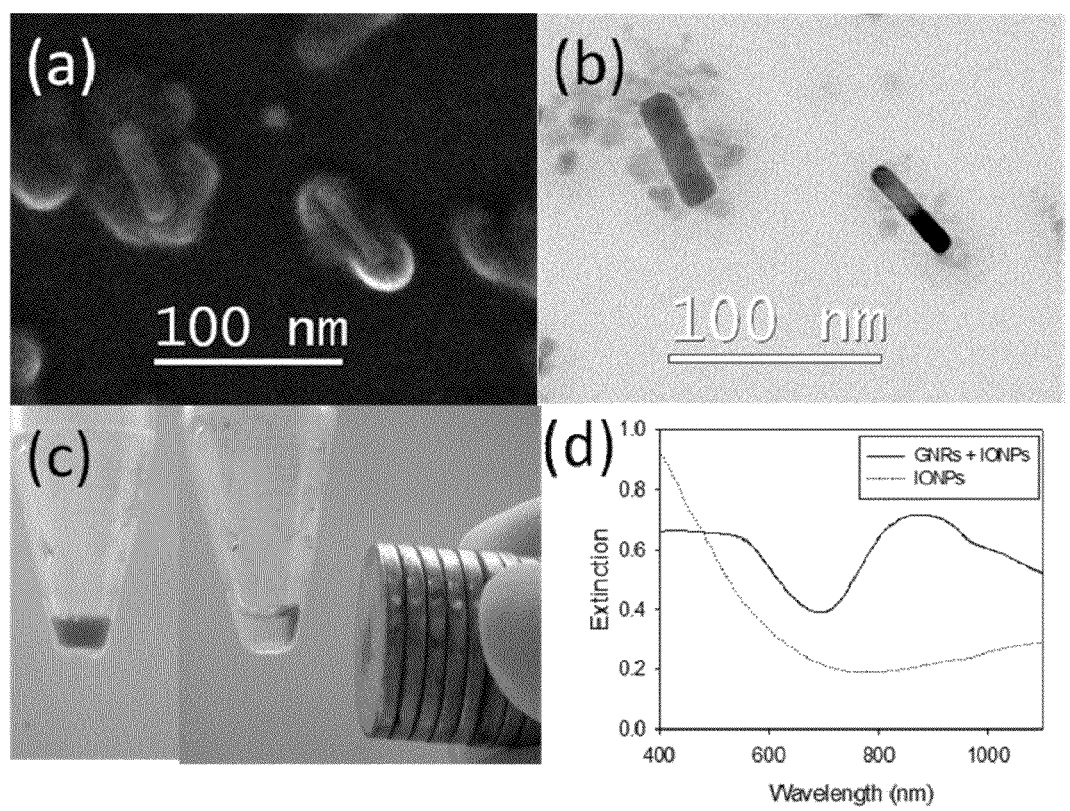
FIG. 3 shows polydopamine-coated gold nanorods (NRs) conjugated to iron oxide nanoparticles (FIGS. 3a and b).

To magnetize the PD-layer, iron oxide nanoparticles were incorporated into the coating. First, iron oxide NPs were formed by mixing $Fe^{2+}$ with $Fe^{3+}$ ions, and magnetism was validated with a magnet. TEM images provide evidence of 10-20 nm sized crystals of iron oxide. These nanoparticles were mixed with PD-coated NRs to form iron oxide-gold nanorod conjugates. Importantly, once these conjugates were purified by magnet and resuspended, the plasmon from the gold NR remained in suspension. TEM was performed and provided evidence of gold NRs conjugated to iron oxide nanoparticle clusters (FIG. 3).

Figure 4:
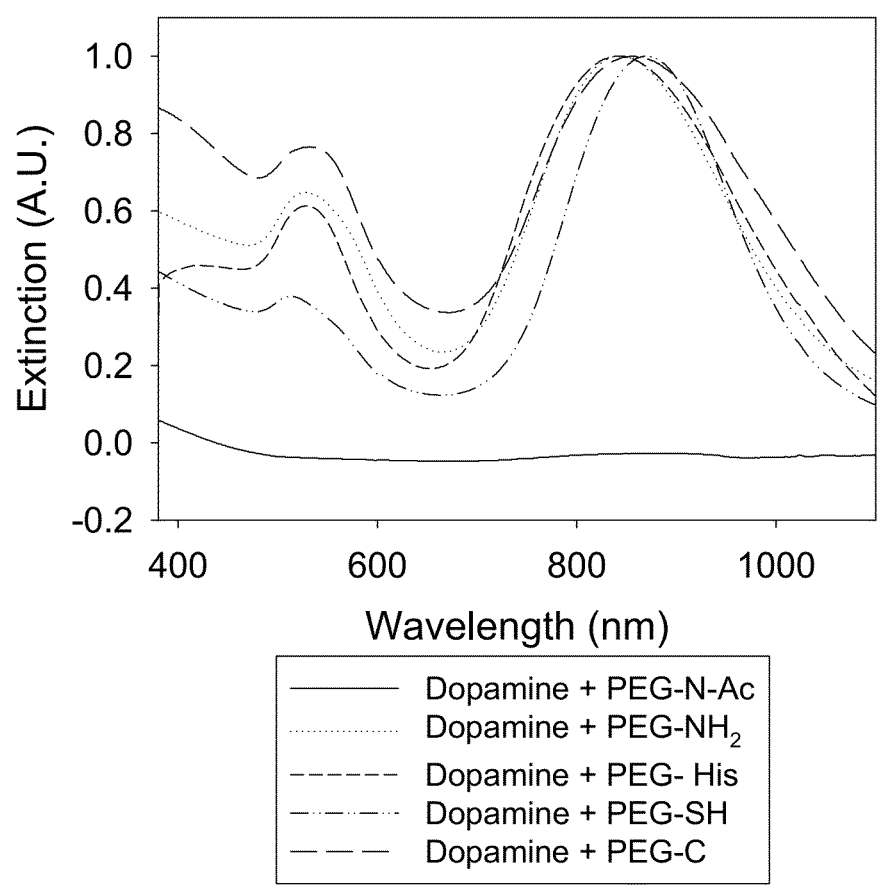
FIG. 4 is a graph showing the results of optical extinction spectroscopy of polydopamine (PD)-coated gold NRs with the addition of different polyethylene glycols (PEGs).
Figure 5:
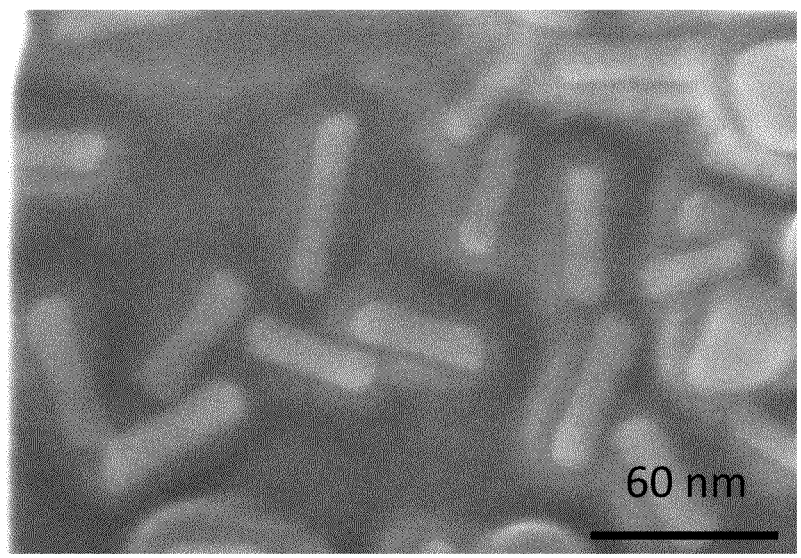
FIG. 5 is an EM image in the secondary electron mode of PD-coated NRs after conjugation with methoxypolyethylene glycol (mPEG).
Figure 6:
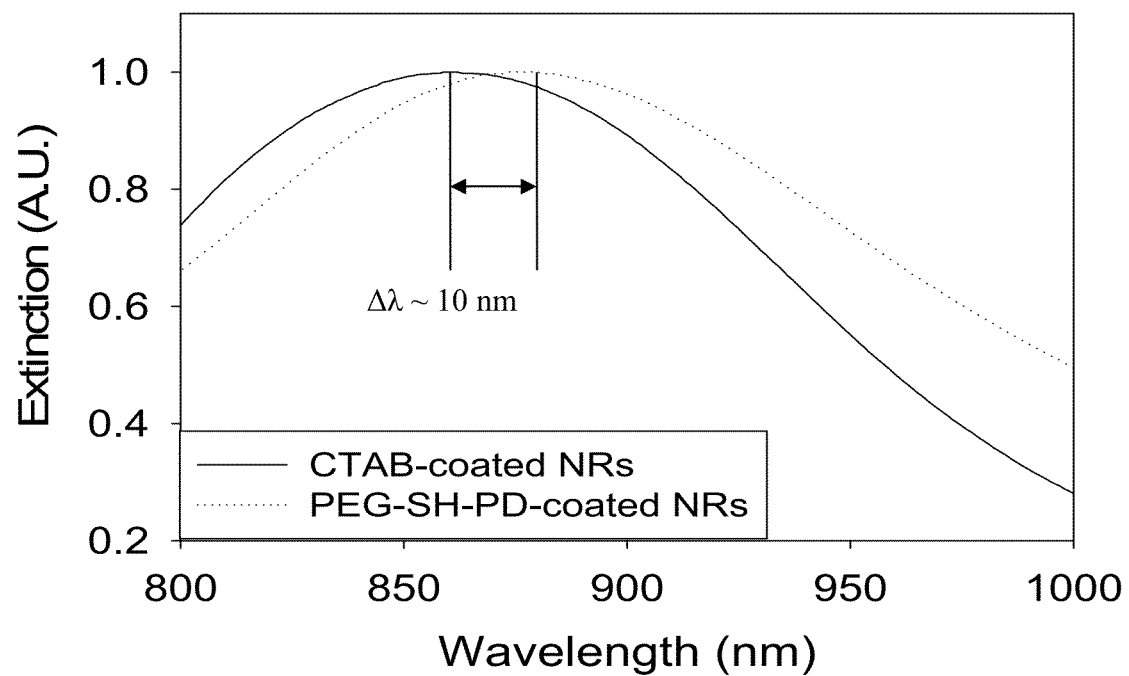
FIG. 6 is a graph showing the results of optical extinction spectroscopy of cetyl trimethylammonium bromide (CTAB)-coated NRs and pegylated-PD-coated NRs. Notice the red-shift after exchanging CTAB with PD.

To further functionalize the PD surface and enhance colloidal stability, PEG molecules containing functionalities reactive to PD were added to the solutions. Importantly, addition of PEGs containing amines, thiols, catechols, and histidines (with imidazole functional group) into suspensions of PD-primed NRs preserved the strong NIR SPR characteristics of the gold NRs after 18 hours of dopamine polymerization and under centrifugation, as compared to controls with unreactive mPEG-NH—Ac (FIG. 4). Pegylated PD-coated NRs were imaged with EM (FIG. 5), which gave evidence of well-dispersed NRs. The red-shifting of the longitudinal SPR of the NRs with PD-coating was preserved with pegylation (FIG. 6). Similar results were obtained with chitosan, pNIPAM, and peptoid coatings.

To further confirm the presence of PD, PEG, and silver on gold NRs, XPS was performed. Spectra of CTAB-coated NRs contained a single C1s peak and a small O1s peak. Contrarily, PD-primed NRs spectra were characterized by a C1s shoulder at higher energies, and significantly higher O1s signal compared to CTAB counterparts. With regard to the presence of PEG, compared to PD-coated NRs, all pegylated PD-coated NRs were characterized by higher C/N ratios, significant O1s signal, and two distinct C1s peaks. PD-coated NRs incubated with silver and PEG had significantly higher Ag/C ratios compared to nonmetalized counterparts, and significant O1s signal compared to CTAB and PD samples. A control spectrum of NRs without PD coated with only PEG-SH gave significantly higher C/N ratios compared to any other samples due to the lack of N1s signal, and O1s signal was pronounced compared to CTAB counterparts.

To conjugate the anti-EGFR antibody ERBITUX® (cetuximab) onto gold NRs, suspensions were initially reacted with dopamine in pH 8.5 for 30 minutes, where red-shifting and broadening of plasmons occurred. Once primed with a thin layer of PD, ERBITUX® (cetuximab) was added to the NR suspension, sonicated for 30 minutes, centrifuged and resuspended in water. Addition of ERBITUX® (cetuximab) infusion to CTAB-coated NRs resulted in loss of the SPR in solution within 20 minutes. When bortezomib was added to PD-coated NRs and centrifuged without the presence of PEG, permanent NR aggregation occurred. Therefore PEG was added after bortezomib in order to provide colloidal stability. Addition of ERBITUX® (cetuximab) after bortezomib also provided transient stability to the NRs for up to one hour.

To interrogate their cell-targeting capabilities, toxicity, and efficacy as optical theragnostic agents, NRs were incubated with OSCC15 cells in vitro, and imaged with bright field microscopy, optical coherence tomography, and 2-photon confocal microscopy. Under bright field, large gold NR aggregates were present on the surface of cells incubated with CTAB-coated NRs. Even larger, micron-sized aggregates were present in PD-primed NR samples. Contrarily, when OSCC15 cells were incubated with pegylated NRs, the presence of NRs could not be detected after washing. To investigate the cellular toxicity of the functionalized NRs, CTAB-coated, PD-primed, and pegylated-PD-primed NRs were incubated with OSCC15 cells in vitro and stained with trypan blue. 100% of cells incubated with CTAB-coated NRs for 30 minutes were stained with trypan blue. Contrarily, there was almost no trypan staining of cells incubated with either PD-primed NRs (0.12%) or pegylated PD-primed NRs (1.7%).

Cells were imaged with OCT. Compared to uncoated control cells, oral cancer cells coated with ERBITUX® (cetuximab)-conjugated silver-coated gold nanorods provided bright signal, presumably from enhanced backscattering in the red-portion of the spectrum. Cells were imaged with a confocal microscope. Importantly, a differential interference contrast (DIC) image could be superimposed on a fluorescent image excited with a NIR laser tuned the SPR of the NRs. A spectrum of the visible emission was acquired between 400 nm and 650 nm. Bright dots associated with NRs could be identified on cellular surfaces.

To interrogate their photothermal properties, NRs were embedded in an alginate gel and irradiated with the Mai:Tai laser. Visible 2-photon excited signal was detected using 2.5% power. The microscope was then focused to an area of high gold NR concentration, the power was turned up to 5% and irradiated for 30 seconds. Gel morphological feature changes occurred during irradiation, eventually giving rise to micron sized cavitation, presumably due to evaporation of some of the aqueous phase of the gel from extreme heating from the NRs. 2-photon excited emission intensity from the gold nanorods coated in either CTAB or PD as a function of incident power was performed. Interestingly, at low power (0.2-1% max power) PD-coated NRs gave statistically significantly greater signal. However, this trend changed and reversed at higher powers (5-10% max power), with PD-coated NRs emitting statistically significantly less signal.

Cellular toxicity experiments were performed to measure toxicity of the PD-coated NRs. In the first set of experiments, gold NRs coated in polydopamine and PEG were incubated with OSCC15 cells. NRs with silver or bortezomib, or controls without additional materials. Controls show minimal toxicity at low concentrations and moderate death at high concentrations. Addition of bortezomib or silver into the NR conjugate significantly increased its toxicity. In the second set of experiments, NRs were conjugated with bortezomib, and then capped with either PEG or the anti-EGFR antibody ERBITUX® (cetuximab). Importantly, toxicity was significantly increased in the NR sample conjugated to both bortezomib and ERBITUX® (cetuximab) compared to all other conditions.

Targeted NP-mediated photothermal therapy was performed as described in the methods. Cells incubated with NRs that were not irradiated did not show significantly different toxicity compared to control. Cells irradiated without the presence of nanorods did show increased death compared to control that was dependent on irradiation time. Importantly, cells incubated with ERBITUX® (cetuximab)-conjugated gold NRs that were also irradiated showed statistically significant enhanced death compared to irradiation alone.

Figure 7:
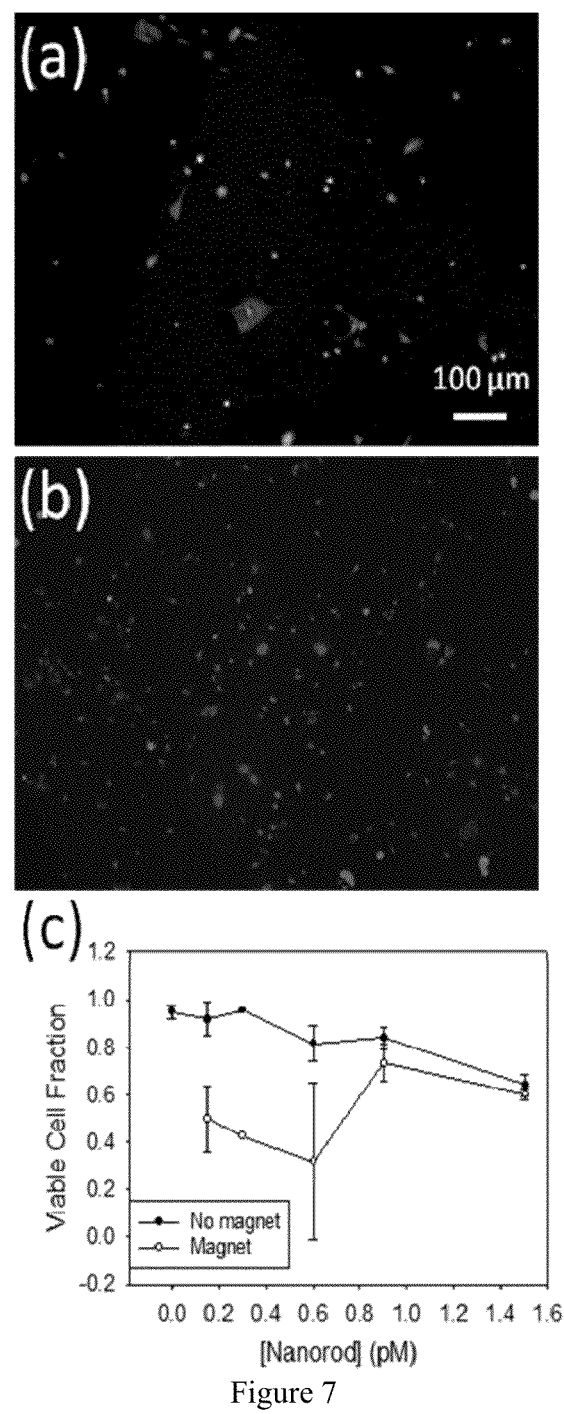
FIG. 7 shows the use of gold nanorods conjugated to iron oxide nanoparticles for cancer therapy: MDA-MB-231 breast cancer cell viability after treatment with gold NR—IONP conjugates and light irradiation, (a) without and (b) with the use of a magnet to attract the conjugates to cells.

Finally, magnetic targeting of conjugates described above, followed by light irradiation, was performed on breast cancer cells in vitro. The magnetic particles were moved to the area of interest using an exterior magnet (magnetic targeting) and irradiated to provide photothermal therapy to cancer cells. Synergistic killing was observed between the use of the magnet and light irradiation (FIG. 7), which was attributed to the increase in NP concentration near cells after the use of the magnet. This increase in particle concentration near cells led to an increase in heating sites upon light irradiation resulting in increased cell death.

Example 2

Polydopamine-Enabled Surface Functionalization of Gold Nanorods for Cancer Cell Targeted Imaging and Photothermal Therapy In this example, we further describe the preparation and anticancer performance of PD coated NIR-active gold NRs. Anti-EGFR antibodies were conjugated to PD coated NRs and their use in targeted photothermal therapy of cancer cells was demonstrated. Antibody functionalized NRs were significantly more toxic to cancer cells in vitro compared to untargeted NRs when irradiated with a broadband light source. The example demonstrates that PD-mediated surface modification is a useful strategy for conjugation of cancer-specific ligands to nanoparticle surfaces, enabling the formation of biofunctional diagnostic and therapeutic metal nanoparticles.

Light sensitive nanoparticles have the potential to be used for anticancer therapy if they can be targeted to surface receptors of cancer cells. The aim of this example was to employ a novel biomimetic strategy for presenting antibodies on surface plasmon resonant gold nanorods (NRs) to target growth factor receptors on cancer cell surfaces for use in photothermal therapy.

A thin conformal coating of the biomimetic polymer polydopamine (PD) was polymerized on the surface of gold NRs in basic aqueous conditions, and epidermal growth factor receptor antibodies (anti-EGFR) were subsequently immobilized onto the biomimetic polymer layer. In vitro cell-binding affinity and near-infrared light activated cell death of oral and breast cancer cells incubated with anti-EGFR functionalized NRs were quantified by optical imaging.

A 5 nm thick PD coating was deposited onto gold NRs, and up to 400 antibodies were subsequently bound per PD-coated NR. NRs functionalized with anti-EGFR antibodies were stable for at least 25 hours in serum containing media, and specifically bound to EGFR overexpressing cells. Illumination of NR targeted cells with near infrared light enhanced cell death compared to dark controls and cells treated with antibody free NRs.

The results demonstrate that PD facilitates the surface functionalization of gold NRs with biomolecules, allowing cell targeting and photothermal killing of EGFR overexpressing cells. Polydopamine can potentially be used with a large variety of nanoparticle platforms and targeting ligands as a strategy for biofunctionalization of diagnostic and therapeutic nanoparticles.

Dopamine hydrochloride, cetyltrimetylammonium bromide (CTAB, 99%), sodium tetrachloroaurate(III) dihydrate ($NaAuCl_4 \cdot 2H_2O$, 99%), sodium borohydride ($NaBH_4$, 98%), ascorbic acid, glycine, and silver nitrate ($AgNO_3$, 99%) were obtained from Sigma-Aldrich (St. Louis, Mo.). The pH value of the glycine solution (0.2 M) was adjusted to 8.0 with 2M sodium hydroxide before use. mPEG-SH (MW=5000) was purchased from Laysan Bio (Arab, Ala.). ALEXA FLUOR® 633 red fluorescent dye goat anti-mouse IgG antibody was purchased from Invitrogen (Carlbad, Calif.). Anti-EGFR antibody was obtained as a commercial infusion (ERBITUX® (cetuximab), 2 mg/ml, ImClone LLC, Bristol-Myers Squibb) from the Robert H. Lurie Comprehensive Cancer Center pharmacy of Northwestern University (Chicago, Ill.). Ultrapure, deionized water (18.2 MΩ·cm) was used to prepare all of the aqueous solutions. OSCC15 cells were acquired from the lab of Dr. David Crowe at the University of Illinois-Chicago. MCF7 and MDA-MB-231 cells were acquired from Dr. Dean Ho at Northwestern University.

Synthesis of Gold NRs.

The synthesis of CTAB-coated gold NRs (CTAB-NRs) was performed according to a slightly modified method previously described in the literature (Huang Yu-Fen et al., Journal of Colloid and Interface Science 301 (2006):145-154). Briefly, CTAB aqueous solution (0.2 M, 5.0 mL, heated to 30° C.) was mixed with 0.5 mM $NaAuCl_4$ (5.0 mL). Ice-cold 0.01 M $NaBH_4$ (0.6 mL) was added to this solution and sonicated for 5 minutes to form a brownish-yellow seed solution. 50.0 mL of 0.2 M CTAB was then gently mixed with 50.0 mL 1.0 mM $NaAuCl_4$ and 0.1 mL 0.1 M silver nitrate to form a growth solution. Ascorbic acid was added to the solution as a mild reductant (78.8 mM, 0.7 mL), followed by addition of 120 μL of the seed solution. After 45 minutes, 100 mL of this gold NR solution was mixed with 100 mL 0.2 M glycine (pH 8.0). This solution was allowed to react overnight without stirring at ambient temperature.

Inductively Coupled Plasma Optical Emission Spectrometry (ICP-OES)

1 mL of the NR stock solution was centrifuged, supernatant removed, and the pellet re-suspended in 500 μL 70% nitric acid. The sample was sonicated in a Branson 2510 sonicator in an ice water bath for 5 hours to dissolve the NRs, after which 154 μL of the resulting solution was added to 4.846 mL pure water and the Au concentration determined in a Varian VISTA-MPX ICP-OES Spectrometer (Varian, Inc. Santa Clara, Calif.) using a calibration curve constructed from 0.1, 0.5, 1, 2, 5, and 10 ppm gold standards (dissolved in 2% nitric acid).

Preparation of PD Coated Gold NRs.

1 mL of CTAB NR suspension was centrifuged and the pellet resuspended in 1.9 mL of a 516 μM dopamine solution buffered to pH 8.5 using 10 mM TRIS buffer. The NR suspension was sonicated for 30 minutes, centrifuged at 9000 rpm for 10 minutes, and the supernatant was removed. Pelleted PD-coated NRs (PD-NRs) were resuspended in 2 mL of ultrapure deionized water, and a UV-Vis-NIR spectrum was acquired to confirm the presence of longitudinal and transverse SPR peaks. Additional centrifugation and removal of supernatant was performed to remove unbound dopamine.

Preparation of PEG Grafted Gold NRs.

For comparison to antibody coated NRs, PEG grafted NRs (PEG-PD-NRs) were prepared by suspending PD-NRs overnight in 1.7 mL 10 mM TRIS buffer (pH 8.5) containing 5 μL of 0.4 mM mPEG-SH at 20° C. PEG grafted NRs were isolated by centrifugation and resuspended in ultrapure deionized water.

Antibody Immobilization on Gold NRs.

PD coated gold NR suspension ($9.1 \times 10^{12}$ NRs/L) was centrifuged and resuspended in 500 μL 10 mM TRIS buffer (pH 8.5). To immobilize the anti-EGFR antibody, 0-350 nM antibody was added to 500 μL PD-NR suspensions and sonicated for 30 minutes. To remove unbound antibodies from the suspension of PD-NRs functionalized with anti-EGFR antibodies (anti-EGFR-PD-NRs), the suspension was then centrifuged at 9000 rpm at 23° C. for 10 minutes, supernatant decanted, and the pellet resuspended in ultrapure water or DMEM. Anti-EGFR-PD-NRs were incubated with 10 nM fluorescent goat anti-mouse IgG secondary antibody, centrifuged, resuspended in 500 μL ultrapure water, and tested in a Synergy 4 Hybrid Multi-Mode Microplate Reader. To quantify antibody density, the fluorescent signal was normalized to NR background fluorescence, and compared to a standard fluorescence curve from free IgG antibody.

Electron Microscopy (EM).

Pelleted NRs (5 μL) were dropped on EM grids (Ted Pella, Redding, Calif.) and allowed to dry overnight in ambient conditions. Transmission EM (TEM), Z-contrast EM, secondary EM (SEM), and energy dispersive X-ray spectroscopy (EDS) spectral imaging were performed on a Hitachi HD-2300 Ultra High Resolution FE-STEM (Hitachi City, Japan).

Optical Spectroscopy.

A Hitachi (Hitachi City, Japan) U-2010 Spectrophotometer was used to acquire optical spectra in a two-beam geometry. To match the NR suspension, 10 mM TRIS buffer, ultrapure deionized water, or DMEM was used for the reference beam. Spectral scans were performed over the 200-1000 nm range of wavelengths in the UV-Visible-NIR region of the spectrum. A deuterium lamp was used for the 200-340 nm UV range illumination and a halogen lamp was used for the visible and NIR illumination. Spectral resolution was 1 nm.

In Vitro Cell Imaging with NRs.

$5 \times 10^5$ oral squamous cell carcinoma 15 (OSCC15), MDA-MB-231 (breast) and MCF7 (breast) cancer cells were grown in tissue culture plates for 3 days. OSCC15 cells were grown in high glucose DMEM (10% FBS, 1% gentamycin), MCF7 cells were grown in high glucose DMEM both with and without insulin (10% FBS, 1% pen/strep), and MDA-MB-231 cells were grown in RPMI-1640 media (10% FBS, 1% pen/strep). 2 mL of trypsin was added to confluent plates of OSCC15 cells, cells were removed, and 400 μL was added to 2 mL of DMEM high glucose media. Cells were centrifuged at 1500 rpm for 5 minutes, supernatant was removed, and 2 mL more media was added. NR suspensions were added to the cells and incubated for 30 minutes. Cells were centrifuged at 1500 rpm for 5 minutes, supernatant was removed, 2 mL of media was added, and finally cells were centrifuged and plated onto glass optical microscopy slides. Bright field images were acquired in a Leica DMRX microscope. To quantify binding, $5 \times 10^4$ MDA-MB-231 cells were grown in 12-well plates and imaged in an optical coherence tomography (OCT) system after incubation with anti-EGFR-PD-NRs for 1 hour. OCT intensity between 750 and 850 nm localized to individual cells was quantified and plotted as a function of antibody concentration.

NR-Mediated Photothermal Therapy.

MDA-MB-231 and OSCC15 cells were cultured in 6-well and 12-well plates and allowed to grow to confluence. Cells were incubated with anti-EGFR-PD-NRs (0.1-20 pM) for 30 minutes-3 hours, washed twice with media, and irradiated with 50 mW NKT photonics SUPERK™ Versa laser source for 5, 10, or 15 minutes; spot size was 1 mm. 1 μL 4 mM calcein and 1 μL 4 mM ethedium bromide was added to each well, and cells were incubated for 15 minutes. Fluorescence microscopy was performed on a Leica DMIRB microscope, with a 250 W maximum Hg arc lamp, and a QIClick detector (QImaging). For each irradiated spot, both calcein-stained cells and ethidium bromide-stained cells were counted, and the % viable cells was calculated (n=1-3 spots).

X-Ray Photoelectron Spectroscopy (XPS).

NR samples were centrifuged, and pellets were deposited onto silicon oxide surfaces and allowed to dry. An Omicron (Taunusstein, Germany) XPS/ESCA Probe was used to acquire spectra. A survey scan over 0-1100 eV binding energy range with 0.5 eV resolution was performed. Higher 0.04 eV resolution spectra were acquired on the identified Au 4 $f_{7/2}$ and 4 $f_{5/2}$, C 1s, O 1s, and N 1s peaks. The binding energy spectral ranges were 82.5-90.5 eV for Au, 283.5-289.02 eV for C, 530.5-536.5 for O, and 395.0-405.0 eV for N. Spectra were calibrated to the C—C peak, located at 284.5 eV.

Quantitative OCT Cell Imaging.

Figure 8:
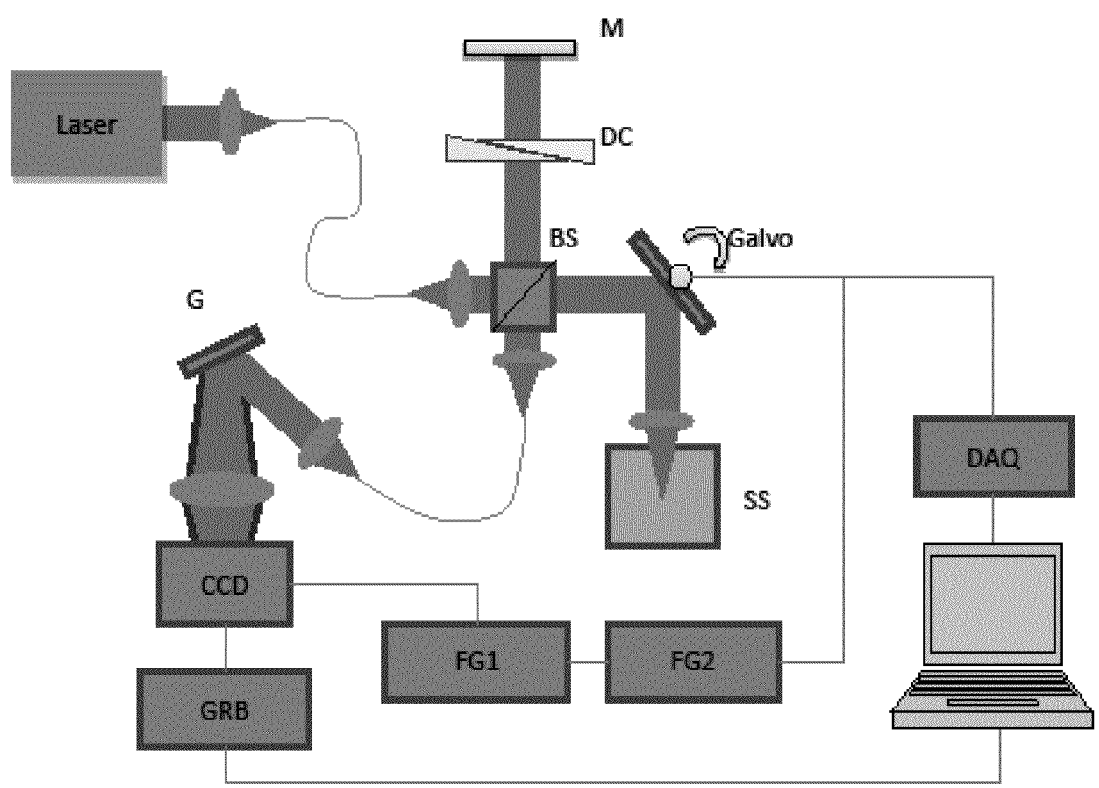
FIG. 8 is a schematic of the optical coherence tomography (OCT) system used for cellular imaging. M=mirror, DC=dispersion compensation, BS=beam splitter, Galvo=galvo mirror, G=holographic diffraction grating, CCD=line scan camera, GRB=frame grabber, FG1,2=function generators, SS=sample stage, DAQ=data acquisition computer.

$5 \times 10^4$ OSCC15, MDA-MB-231, and MCF7 cells were incubated with anti-EGFR-PD-NRs in media at 37° C. for 1 hour, washed with media twice, and imaged in an optical coherence tomography (OCT) imaging system (FIG. 8). A low coherence laser beam output from a supercontinuum source (SUPERK™ Versa, NKT photonics) was coupled into a single mode fiber and collimated into an open space Michelson interferometer. A beam splitter divided the beam into sample and reference arms and a well corrected microscopic objective created a 5 mW focused illumination with effective NA=0.04. A galvo mirror guided the beam before the objective to realize the B-scan. The reference arm included a reflecting mirror, a neutral density filter, and a quartz plate for dispersion compensation. The reflected beams from two arms were recombined by the beam splitter and coupled into a spectrometer through a single mode fiber.

Inside the spectrometer, the interfered beam was collimated by an f=30 mm lens and directed to a holographic diffraction grating (1200 grooves/mm). A commercially available lens (Nikon f=135 mm) focused the dispersed beam on a 2048 pixel line scan camera (e2v) to record the spectrum from 650 nm to 820 nm resulting in an axial resolution of ~2 µm in air. Two function generators (Agilent) were synchronized to drive the galvo scanning mirror and provide exposure trigger to the camera. The frame rate was 5 fps to maximize the signal to noise ratio. Cells were identified in the image, and the average pixel intensity per cell between 750-850 nm was quantified to determine NR density.

Quantification of IgG Antibody Density on Gold NRs.

Due to the difficulties of quantifying the amount of EGFR antibody bound to the NR surface, the following approach was used to provide an estimate of bound antibody. 0-350 nM goat anti-mouse IgG antibody conjugated with ALEXA FLUOR® 633 red fluorescent dye (Invitrogen) was incubated with PD-NRs in 10 mM TRIS buffer (pH 8.5) for 30 minutes in 500 µL aliquots. Samples were centrifuged, supernatant was removed, and pellets were resuspended in identical 500 µL volumes. The fluorescent intensities of the supernatant solutions were compared to a standard curve in a Synergy 4 Hybrid Multi-Mode Microplate Reader to quantify the concentration of unbound antibodies.

To quantify the concentration of bound antibody, the fluorescent intensities of the resuspended pellets were normalized to the background intensity from PD-NRs without antibody addition and compared to a standard curve. The number of antibodies per NR was determined by comparing the concentration of bound antibody to the NR concentration (calculated from the gold atom concentration from ICP-OES and gold nanoparticle size from TEM assuming a right circular cylinder shape as described in main text).

Figure 9:
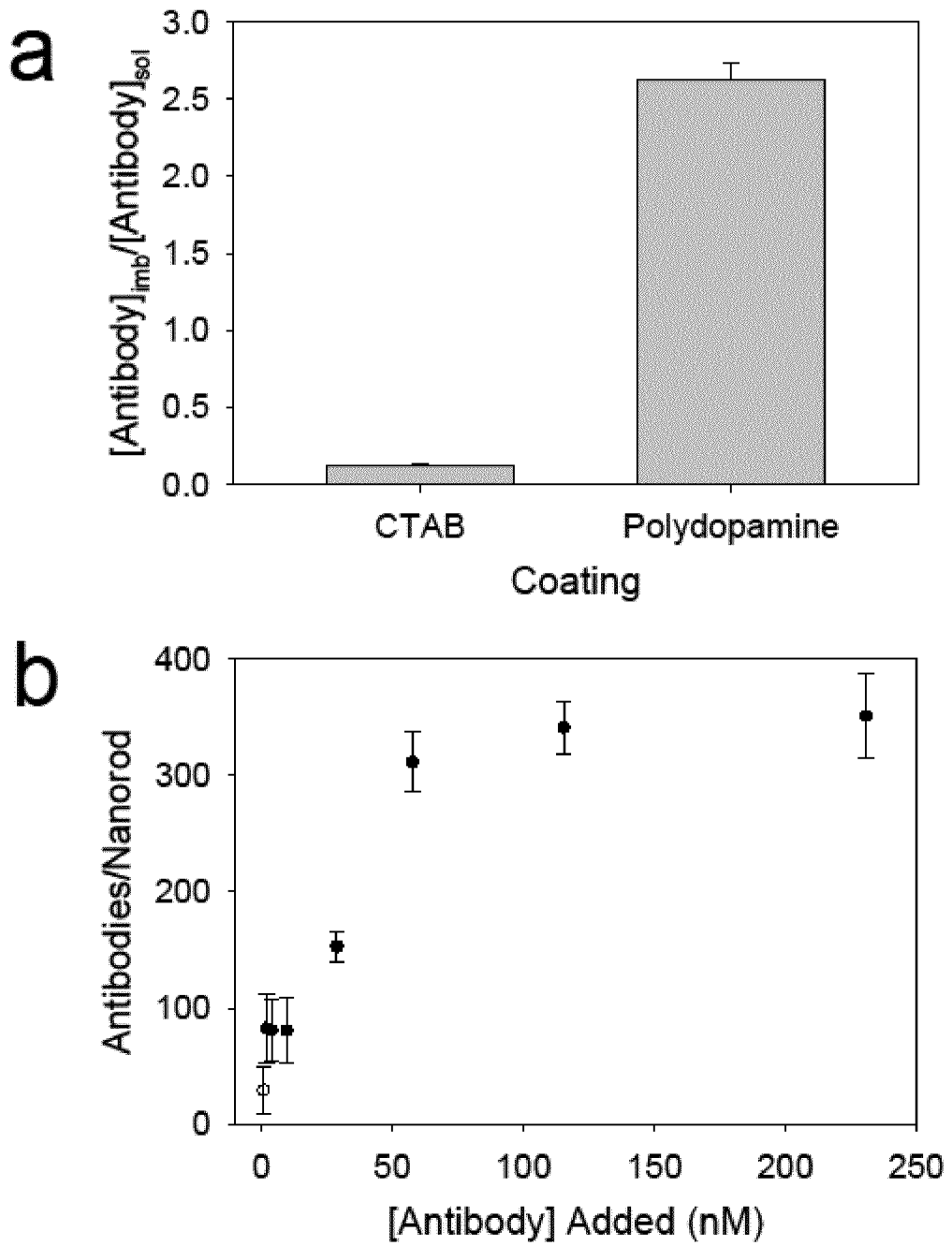
FIG. 9 shows quantification of IgG antibody density on gold nanorod (NR) surface. (a) Ratio of the concentration of antibody immobilized on gold NR surface compared to the concentration of unbound antibody in solution.

After centrifugation and separation of the NRs from the supernatant solution, the ratio of immobilized to free antibody was 2.6 for PD-NRs, compared to 0.12 for CTAB-NRs (FIG. 9a), corresponding to a 22-fold increase in antibody immobilization on PD-coated NRs compared to CTAB-coated NRs. Further, the number of antibodies per NR was tuned by varying the concentration of antibody added to a constant PD-NR concentration, up to a surface density of 350 per NR (FIG. 9b).

Results.

Figure 10:
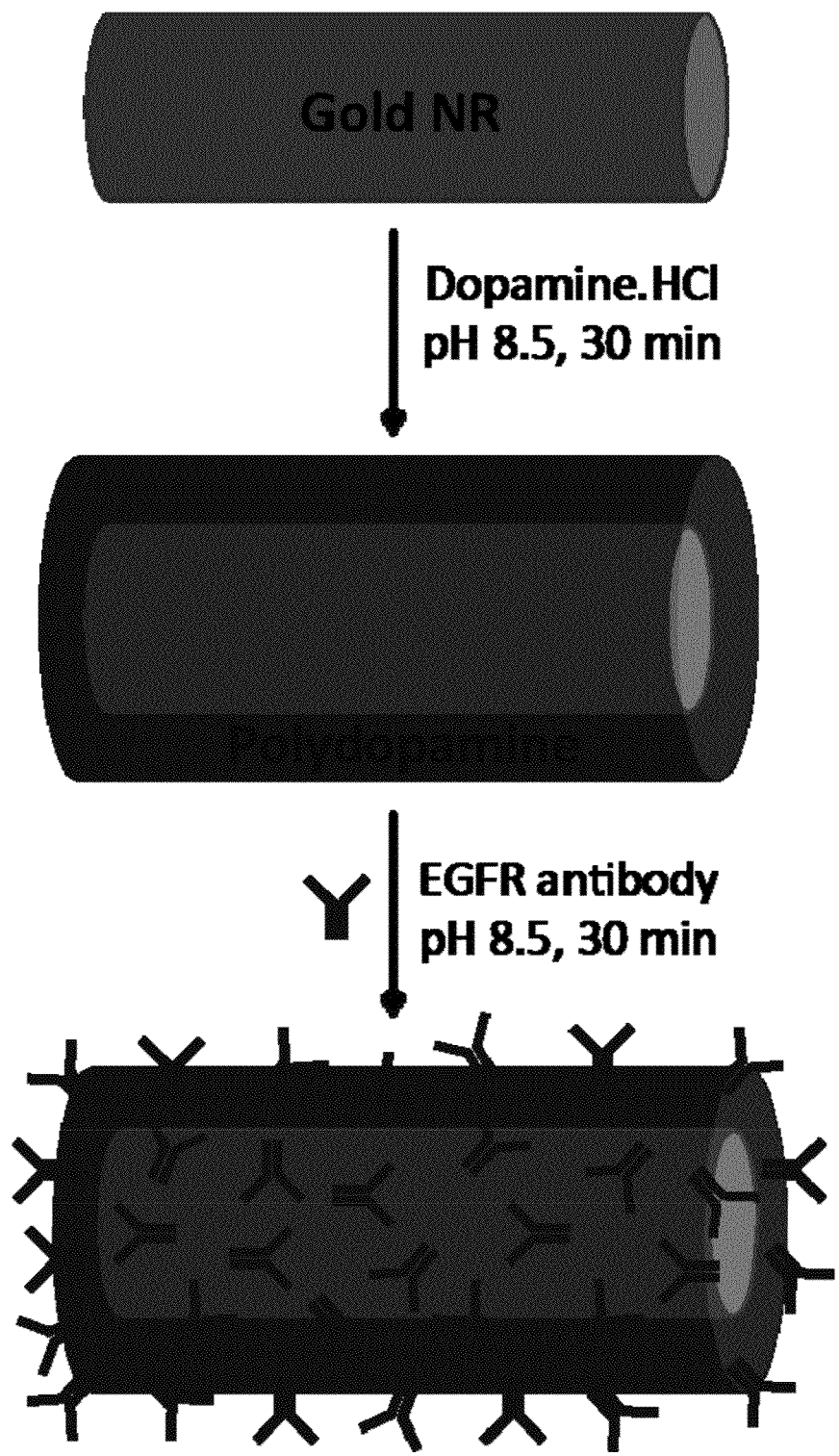
FIG. 10 is a schematic illustration of the preparation of EGFR antibody-conjugated gold NRs (Anti-EGFR-PD-NRs) using a polydopamine 'primer' coating.
Figure 11:
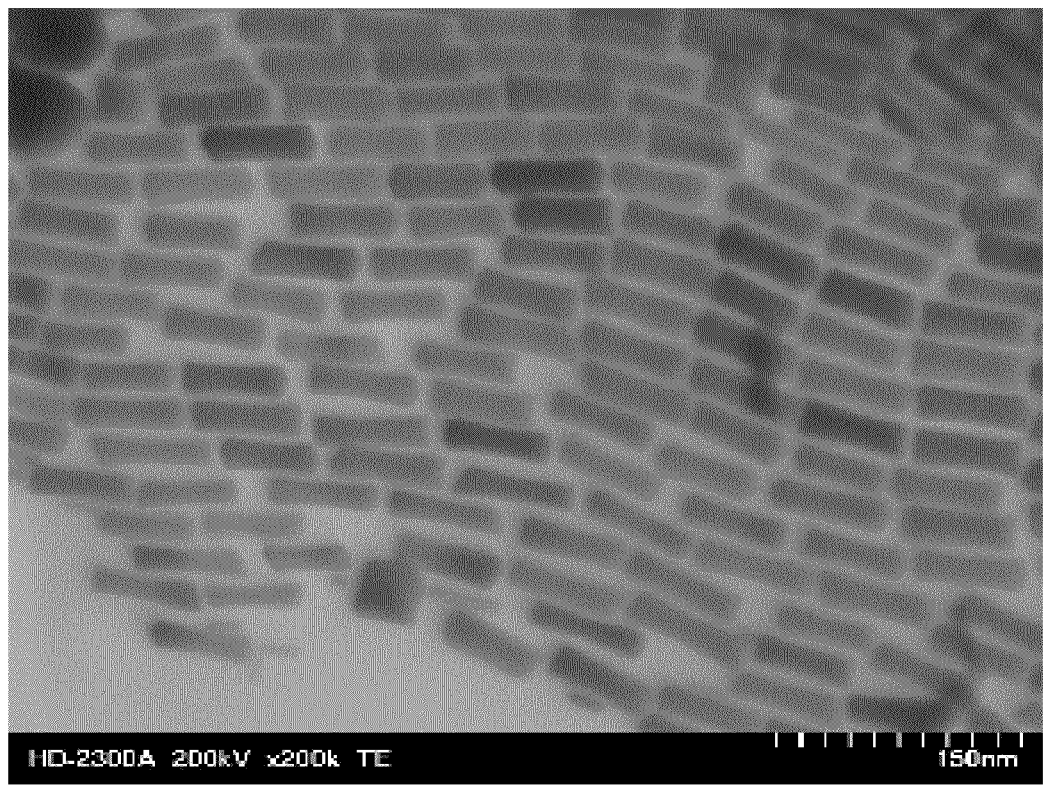
FIG. 11 is a TEM image of cetyl trimethylammonium bromide (CTAB) stabilized gold nanorods.

In this example, a general strategy was used to immobilize antibodies onto gold NR surfaces through an intermediate PD layer (FIG. 10). First, high yield (>95%) CTAB-NRs were synthesized using established protocols. The apexes of the transverse and more intense longitudinal extinction peaks of CTAB-NRs were located at 520 nm and 783 nm, respectively, and were stable during storage in excess CTAB at room temperature for at least 6 months. CTAB-NRs were imaged by TEM and had an average length of 62±6 nm and width of 17±3 nm (n=123) (FIG. 11). 0.294±0.013 mg/L of gold was detected in the NR suspension treated with nitric acid described in the methods. Taking this concentration, the density of gold, and assuming a right circular cylinder shape, the gold NR concentration in the initial stock suspension was determined to be $1.81 \times 10^{13}$ NRs/L (30.1 pM).

Figure 12:
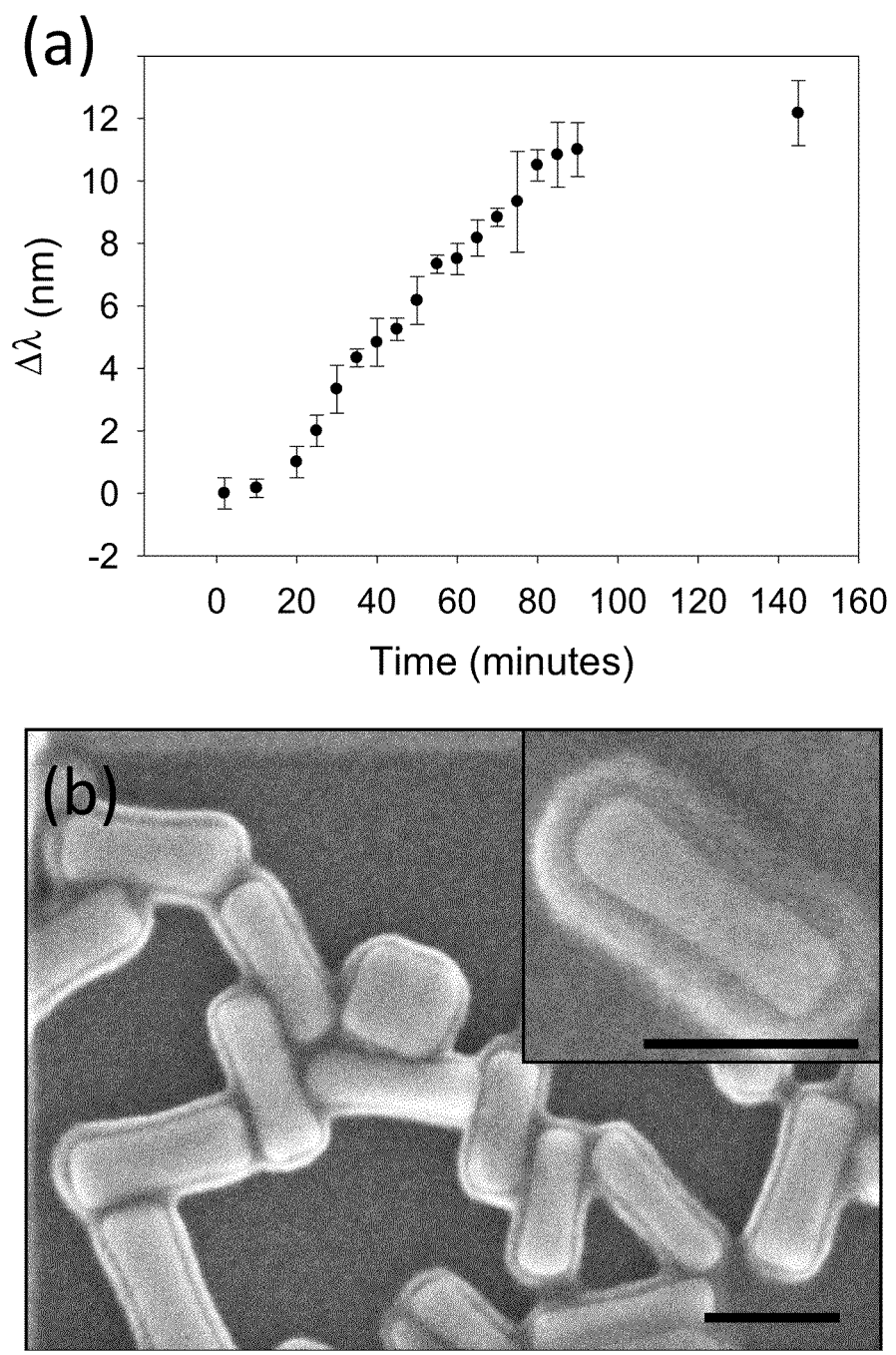
FIG. 12 shows (a) optical extinction spectroscopy of gold NRs stabilized with cetyltrimethylammonium bromide (CTAB) before and after reaction with 555 µM dopamine in pH 8.5 for 30 minutes, (b) Secondary electron microscopy of gold NRs coated in polydopamine (PD-NRs).

PD deposition was accomplished by dispersion of CTAB-NRs in an alkaline dopamine solution, upon which spontaneous deposition of PD onto NRs accompanied by displacement of the CTAB ligand was observed. UV-Vis extinction spectra acquired during this process revealed a linear red-shift over time (FIG. 12a), corresponding to a PD coating of 5 nm thickness as observed by secondary electron microscopy (FIG. 12b).

Figure 13:
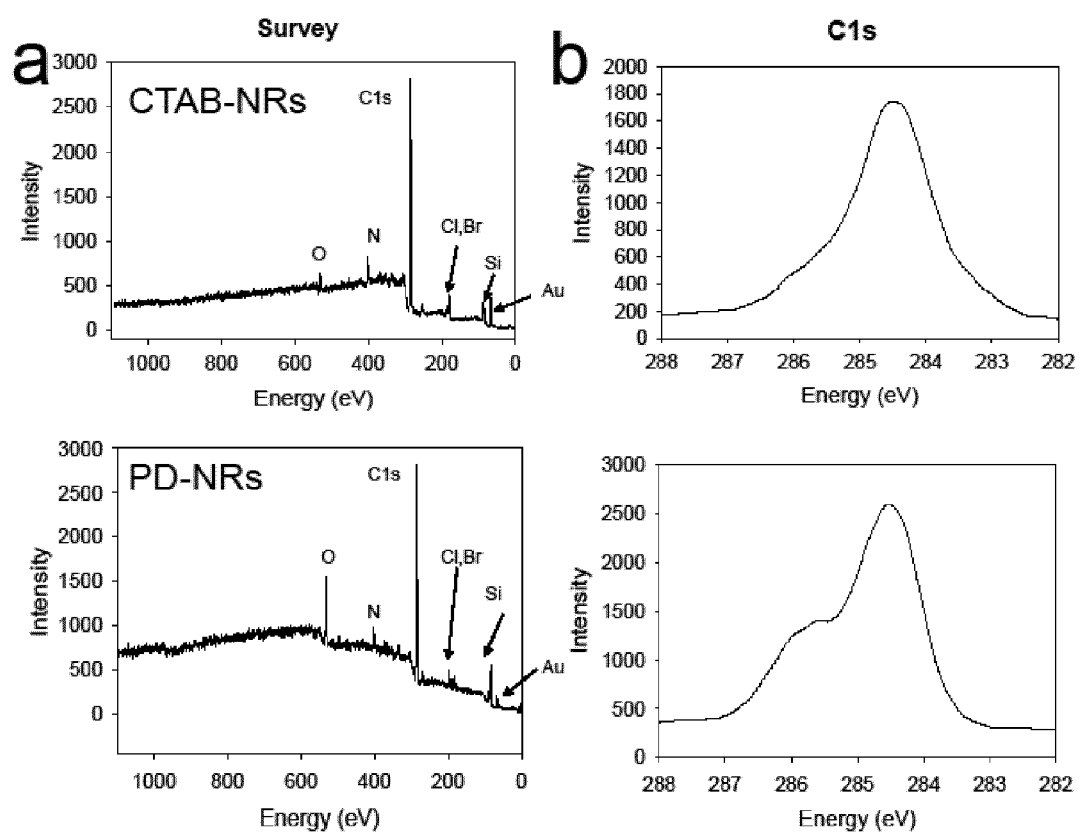
FIG. 13 shows the results of X-Ray photoelectron spectroscopy of gold NR samples on silcon surfaces.

To further confirm the presence of PD on the surface of gold NRs, XPS was performed (FIG. 13). In contrast to the single C1s peak observed from CTAB-NRs, high resolution C1s spectra of PD-NRs were characterized by a peak centered at 284.5 along with a significant shoulder toward higher energies representative of C—O and C—N bonds in the PD.

Figure 14:
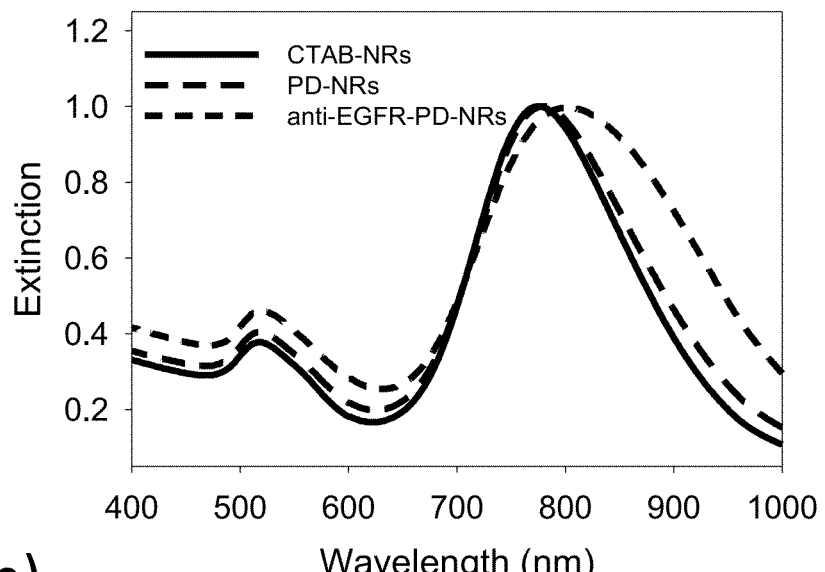
FIG. 14 shows anti-EGFR antibody immobilization onto polydopamine-coated NRs (PD-NRs). (a) UV-Vis extinction of PD-NRs before and after anti-EGFR antibody conjugation ([NR]=0.0150 nM); (b) Stability of longitudinal plasmons of PD-NRs functionalized with anti-EGFR antibodies in serum-containing DMEM.
Figure 14:
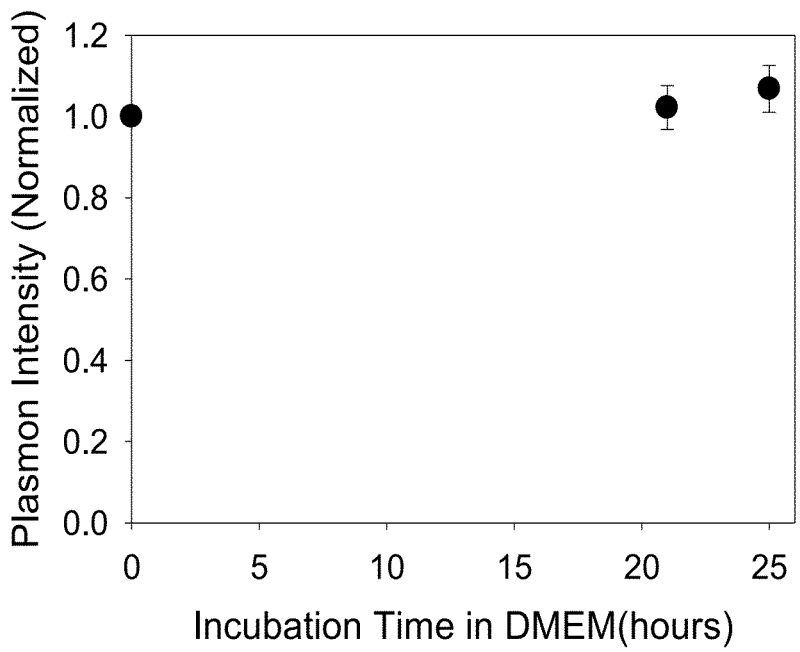

To provide clinically relevant anticancer functionality, anti-EGFR antibodies were immobilized onto PD-NRs at pH 8.5 for 30 minutes. Red-shifting and broadening of the longitudinal SPR occurred during conjugation (FIG. 14a). To further confirm the presence of the antibody on the gold NR, anti-EGFR-PD-NRs were stained with a secondary anti-mouse IgG antibody, and fluorescent signal representative of an antibody monolayer (~400 antibodies/NR) on the PD coating was detected. Stability of the anti-EGFR-PD-NRs was tested in DMEM media over the span of 24 hours, with no statistical loss in SPR intensity observed (FIG. 14b).

Figure 15:
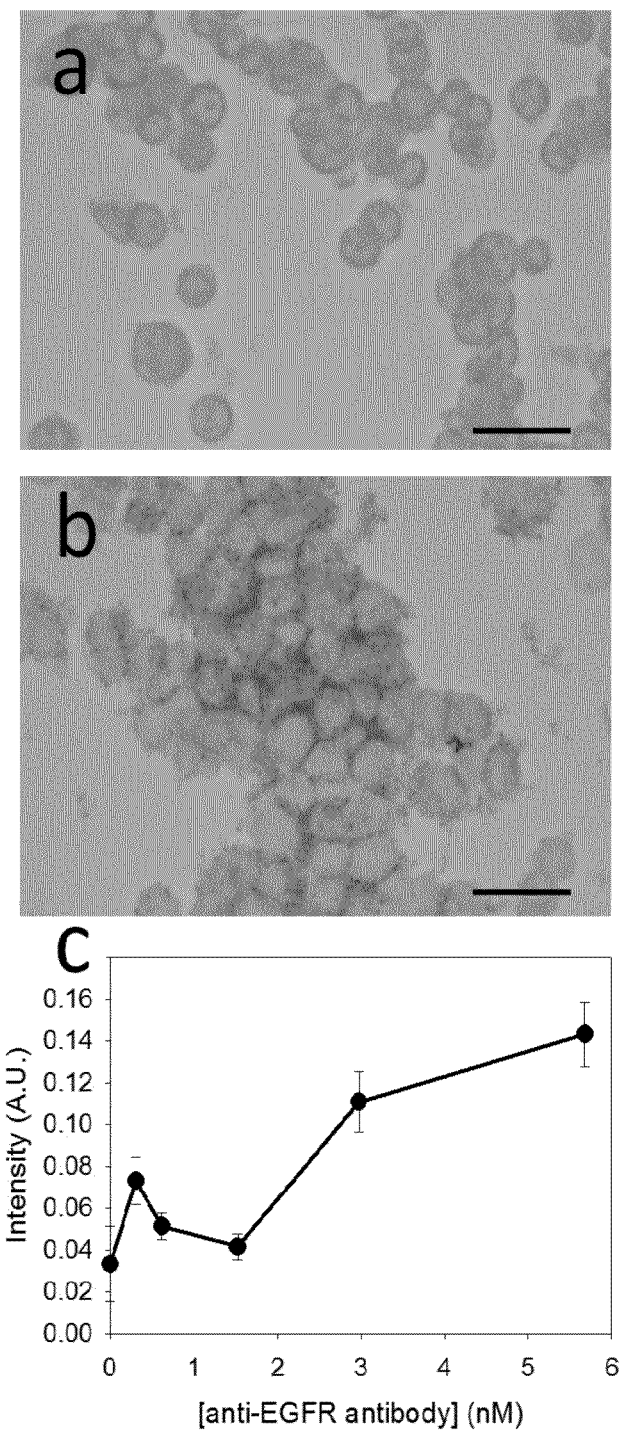
FIG. 15 shows optical imaging of cells incubated with NRs. Bright field light microscopy images of OSCC15 oral cancer cells incubated with (a) PEG-PD-NRs, and (b) anti-EGFR-PD-NRs. Scale bars in a and b=20 µm. (c) OCT intensity from individual MDA-MB-231 breast cancer cells as a function of anti-EGFR-PD-NR concentration.

To explore EGFR targeting, anti-EGFR-PD-NRs were incubated with two cancer cell lines characterized by high EGFR expression, OSCC15 oral cancer cells[65] and MDA-MB-231 breast cancer cells (Fitzpatrick, 1984). Optical microscopy revealed that anti-EGFR-PD-NRs were visibly interacting with cells, whereas NRs were not visible on cells treated with PEG-PD-NRs in identical conditions (FIGS. 15a and b). Further, a concentration dependent increase in NIR light intensity (750 nm-850 nm) localized to cellular structures was observed in MDA-MB-231 cells incubated with anti-EGFR-PD-NRs (FIG. 15c), with a 4.1 fold increase in light intensity observed at an antibody concentration of 5.7 nM ([NR]=14 pM). No increase in intensity was observed in low-EGFR expressing MCF7 breast cancer cells incubated with anti-EGFR-PD-NRs (data not shown).

Figure 16:
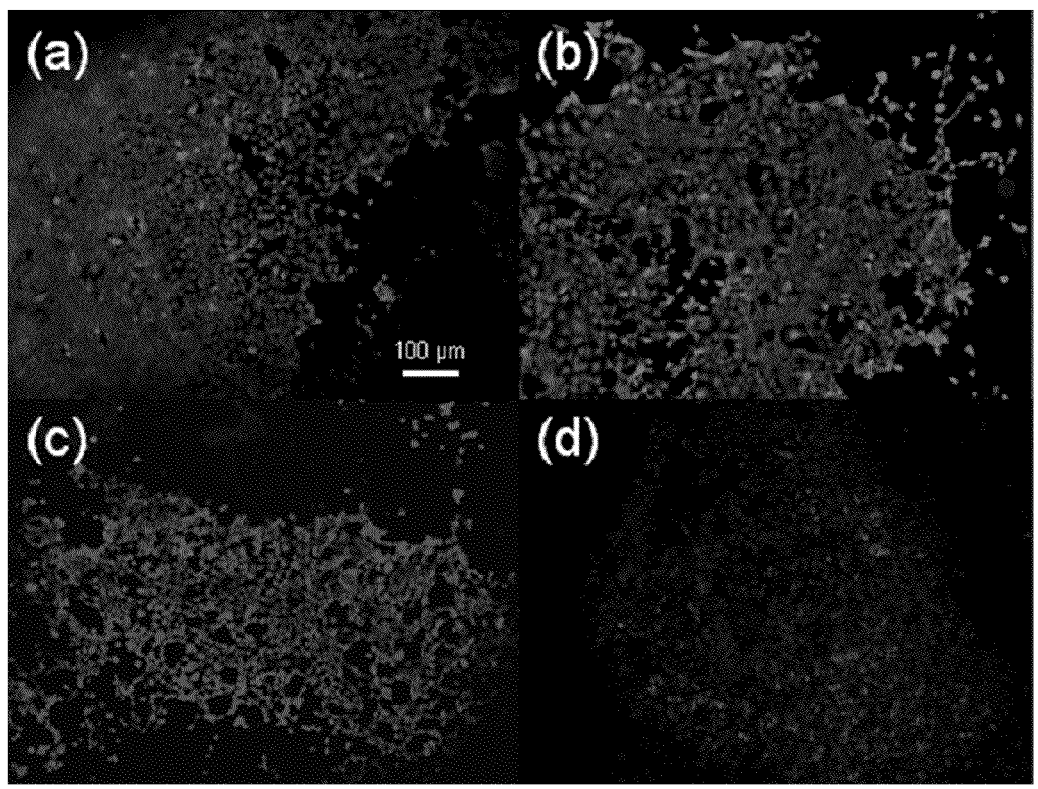
FIG. 16 shows cell images resulting from photothermal therapy of OSCC15 cells. Images of cells treated as follows: (a) cells irradiated for 5 minutes in the absence of NRs; (b)

Next, we demonstrated photothermal therapy of OSCC15 cells targeted with anti-EGFR-PD-NRs (FIGS. 16 and 17). In control experiments, no toxicity of cells was observed immediately after irradiation in the absence of NRs (FIG. 16a), or in cells incubated with anti-EGFR-PD-NRs without irradiation (FIG. 16b). Whereas cells incubated with 9.92 pM PEG-PD-NRs and then irradiated maintained 91% viability (FIG. 16c), viability of cells incubated with the same concentration of anti-EGFR-PD-NRs and then irradiated decreased to 24% (FIG. 16d). Thus, cells targeted with anti-EGFR-PD-NRs and irradiated with light were killed more efficiently than any other treatment (FIG. 17a).

NR-mediated photothermal therapy was also performed on MDA-MB-231 breast cancer cells, which exhibit overexpression of EGFR. Like OSCC15 cells, MDA-MB-231 cells treated with anti-EGFR-PD-NRs but not irradiated maintained high viability at all time points tested in this study, whereas irradiation significantly decreased viability in a NR-concentration dependent manner (FIG. 17b). After 5 minutes of irradiation, cells not treated with NRs were 79% viable; in the same conditions, cells incubated with anti-EGFR-PD-NRs were between 37% and 70% viable depending on the NR concentration. Further, longer incubation times with anti-EGFR-PD-NRs provided enhanced toxicity when coupled with irradiation (FIG. 17c).

Discussion.

Gold NRs have shown promise as contrast agents and photothermal therapeutic agents in vitro and in vivo. However, a versatile chemical approach is needed to couple the optically functional metal nanoparticles with a broad range of biologically specific molecules in physiological environments to fully realize their biomedical potential. Catecholamine molecular adhesives, inspired by the protein glues of mussels that adhere to wet, chemically heterogeneous surfaces in diverse aqueous environments, can be exploited to functionalize metal nanoparticle surfaces for biomedical applications. PD is perhaps the simplest form of a mussel mimetic coating in terms of ease of use and versatility, depositing spontaneously as a thin conformal coating on surfaces by taking advantage of a rich repertoire of chemical interactions with surfaces. The thickness of PD coatings as well as their deposition rate can be easily tailored through deposition conditions such as pH and dopamine concentration.

PD deposition on the gold NR surface was indicated by a red-shift of the longitudinal SPR (FIG. 10a), XPS analysis showing a C1s shoulder representative of C—O and C—N bonds in the PD coating (FIG. 13), and secondary EM images revealing a 5 nm thick PD layer surrounding gold NRs (FIG. 12b). A multivalent interaction occurs between PD and the metal NR surface, likely including pi electron, electrostatic, and metal coordination interactions, giving rise to a robust cohesive coating that mimics the molecular adhesives evolved in mussels that thrive in turbulent sea environments with similar characteristics to high ionic strength, high flow in vivo conditions.

PD coatings further serve as a platform or 'primer' onto which further surface modifications can be performed. In this study, PD was used in this way to provide a versatile chemical interface for conjugation of antibodies and other biomolecules onto the surface of NIR-active gold NRs for targeting cancer cells. When coupled to metal nanoparticles, antibodies offer complementary biological functions like specific binding to human cell surface receptors associated with cancer phenotypes such as EGFR, the human epidermal growth factor receptor 2 (HER2), glucose transporters like GLUT1 that are upregulated under glycolysis, and mucin receptors such as MUC1.

To quantitatively characterize the general immobilization of antibodies onto PD-NRs, fluorescently-tagged IgG antibodies were incubated with PD-NRs in alkaline conditions. A 22-fold increase in immobilized antibody was observed compared to CTAB-NRs (FIG. 9a), illustrating the advantage of using PD for biomolecule conjugation to surfaces. The number of antibodies per NR could be controlled between 8 and 350 (FIG. 9b), the latter number corresponding to an antibody monolayer immobilized onto a 5 nm thick PD layer surrounding a 62 by 17 nm gold NR.

To create an anticancer NR using the biomimetic PD approach, anti-EGFR antibodies were immobilized onto the PD layer. Immobilization of anti-EGFR antibody onto gold NRs produced a red-shift and broadening of the longitudinal and transverse plasmon bands of the gold NR (FIG. 14a).

Anti-EGFR-PD-NRs were stable in serum-containing medium for at least 25 hours (FIG. 14b), avoiding nonspecific interactions and NR aggregation and facilitating specific targeting to EGFR-expressing cells (FIG. 15) where they provided a light activated therapeutic response (FIGS. 16 and 17).

Anti-EGFR-PD-NRs added to cell culture media strongly interacted with EGFR-expressing cells (FIG. 15), producing a 4-fold enhancement of the OCT signal in the NIR range (FIG. 15c) due to the backscattering from gold NRs bound to cells. OCT signal increases were detected as low as 0.3 nM antibody, significantly lower than the dissociation constant ($K_d$) values for free antibody of 4.54 nM, which could be caused by multivalent enhanced binding through multiple antibodies on a single NR. In contrast, OCT intensity from MCF7 cells lacking high EGFR expression was not enhanced by incubation with anti-EGFR-PD-NRs at any of the concentrations tested, implying that the increase in intensity from the MDA-MB-231 cells upon incubation with anti-EGFR-PD-NRs was due to binding of NRs to cells through a specific antibody-receptor interaction.

In the future, quantitative EGFR-targeted spectroscopic imaging with anti-EGFR-PD-NRs could be used to help identify high risk, EGFR-expressing phenotypes with bright field microscopy of ex vivo biopsies or OCT of tumors in vivo. Due to their sub-100 nm particle size, targeting specificity, and PD interface that decreases in vivo toxicity and immunological response, anti-EGFR-PD-NRs should be capable of intravenous in vivo administration in an effort to increase antibody delivery efficiency to tumor sites through the enhanced permeability and retention (EPR) effect that occurs in leaky tumor vasculature.

Once bound to cancer cells, irradiation with light transforms NRs into potent therapeutic agents, providing a second therapeutic mechanism in addition to the current antibody-based EGFR inhibition. Our results indicate that light irradiation of anti-EGFR-PD-NRs targeted to oral or breast cancer cells provided enhanced therapeutic efficacy compared to control treatments. The observed toxicity arising from NIR irradiation of anti-EGFR-PD-NRs bound to OSCC15 and MDA-MB-231 cells is likely due to direct thermal damage caused by cavitation upon irradiation, as heating of gold NRs can produce extreme local temperatures at the NR surface and to yield bulk temperature increases in the range of 10 to 50° C. Alternatively, toxicity may arise from secondary effects associated with hyperthermia such as calcium influx-induced membrane blebbing. Further studies will be necessary to elucidate the mechanism of cell death produced by light irradiation of anti-EGFR-PD-NRs.

The responses observed in both oral and breast cancer cells demonstrate the clinical potential of anti-EGFR-PD-NRs toward EGFR-specific pathologies, however the strategy is broadly applicable to any antibody and could in the future be used to target other cancer-related cell surface receptors, such as HER2, GLUT1, and MUC1. Furthermore, the versatility of the PD surface modification strategy facilitates highly tailored surface modifications that include multiple biological ligands, passivating polymers like PEG, and other targeting ligands such as peptides and DNA aptamers.

Finally, we note that our approach could prove to be a useful adjunct to existing surgical oncology practices. For example, we envision that NIR irradiation of NRs could be used as a complement to current tumor excision techniques to decrease the likelihood of recurrence. Employing NRs as opposed to spherical gold nanoparticles shifts the relevant wavelengths into the NIR range, which penetrates far deeper into tissue than visible light, allowing in principle noninvasive activation of NRs for treatment of currently inoperable tumors. Since therapeutic efficacy was observed even at the lowest concentration tested (62.5 pM antibody, 0.21 pM NR), systemic in vivo administration of NRs could provide sufficient dose to tumor sites to observe a light-induced therapeutic response.

PD offers a versatile chemical interface for coupling of biological molecules with metal nanoparticles, as illustrated by the synthesis of PD-functionalized gold NRs conjugated with anti-EGFR antibody. The anti-EGFR-PD-NRs were stable in serum containing media and selectively bound to cells expressing EGFR. Although the anti-EGFR-PD-NRs were not toxic to cells in the absence of light, significant photo-induced toxicity of breast and oral cancer cells was observed upon exposure to NIR light. In the future, this biomimetic strategy can be expanded to include other functional nanomaterials like superparamagnetic iron oxide, and other targeting and therapeutic moieties such as small molecule drugs and other cell-surface targeting antibodies, in order to form multifunctional agents for specific diagnosis and combination therapy for complex resistant diseases such as heterogeneous cancers and antibiotic resistant bacteria.

Example 3

Plasmonic Heating Enhances Antibacterial Effect of Silver-Coated Gold Nanorods

In this example, polydopamine (PD) is used to coat gold nanorod (NR) surfaces and deposit silver in order to tune SPRs and provide antibacterial functionality. Antibacterial antibodies are reacted to PD surfaces through catechol redox reactions to provide biologically-specific targeting to bacterial cell walls. These multifunctional biomimetic metal NRs target both gram-negative $E.$ $coli$ and gram-positive $S.$ $epidermidis$, providing contrast in optical imaging. Finally, light irradiation provides a potent therapeutic response to bacteria targeted with metal NRs, providing multiple mechanisms of action that includes cell-targeted photothermal heating and silver-based toxicity. The example demonstrates that catecholamine-based interfaces have the potential to form a broad range of biotargeted metal NPs for the diagnosis and treatment of antibiotic resistant bacterial infections and other diseases.

In this example, we use a catecholamine-based approach to control the SPR and biological functionality of colloidal metal NPs with shape and compositional control for multifunctional photothermal treatment of bacterial cells. PD is used to combine a NIR-active gold NR, silver, and antibacterial antibodies to form multicomponent antibacterial photothermal agents (FIG. 18). PD adheres strongly to gold NR surfaces by forming a conformal cross-linked interface, immobilizes silver onto gold NRs in a controlled manner, and covalently reacts to antibodies to provide biofunctionalization. When functionalized with the proper antibody and irradiated with light, these metal NRs efficiently killed both gram-positive $Staphylococcus$ $epidermidis$ ($S.$ $epidermidis$) and gram-negative $Escherichia$ $coli$ ($E.$ $coli$). More broadly, the biomimetic chemistry of PD offers a versatility that may prove useful in the formation of multifunctional antibacterial metal NPs that provide photothermal therapeutic treatment in the ongoing arms race between microbes and man.

Dopamine hydrochloride, cetyltrimetylammonium bromide (CTAB, 99%), sodium tetrachloroaurate(III) dihydrate ($NaAuCl_4.2H_2O$, 99%), sodium borohydride ($NaBH_4$, 98%), ascorbic acid, glycine, and silver nitrate ($AgNO_3$, 99%) were obtained from Sigma-Aldrich (St. Louis, Mo.). The pH of 0.2 M glycine solution was adjusted to 8.0 with 2M sodium hydroxide before use. Heterobifunctional PEG (methoxy-PEG-SH, mPEG-SH, MW=2 kDa) was purchased from Laysan Bio (Arab, Ala.). Antibody against endotoxin of gram negative bacteria, and antibody against lipoteichoic acid of gram-positive bacteria were purchased as a solution (0.1 mg/ml) from MyBioSource (San Diego, Calif.). SYTO® 9 green fluorescent nucleic acid stain and propidium iodide were purchased from Invitrogen (Grand Island, N.Y.). $Staphylococcus$ $epidermidis$ (RP62A) and $Escherichia$ $coli$ (J5 mutant, 43745) bacteria were purchased from ATCC (Manassas, Va.).

Gold NR Synthesis.

Gold NRs with longitudinal SPRs in the NIR portion of the electromagnetic spectrum were synthesized in surfactant-containing water solutions according to previously described protocols (Y. F. Huang et al., Journal of Colloid and Interface Science 301 (2006): 145-154) and summarized here. Aqueous CTAB solution (0.2 M, 5.0 mL, heated to 30° C.) was mixed with 0.5 mM $NaAuCl_4$ (5.0 mL). Ice-cold 0.01 M $NaBH_4$ (0.6 mL) was added to this solution and sonicated for 5 minutes to form a brownish-yellow seed solution. 50.0 mL of 0.2 M CTAB was then gently mixed with 50.0 mL 1.0 mM $NaAuCl_4$ and 0.1 mL 0.1 M silver nitrate to form a growth solution. Ascorbic acid was added to the solution as a mild reductant (78.8 mM, 0.7 mL), followed by addition of 120 µL of the seed solution. After 45 minutes, 100 mL of this gold NR solution was mixed with 100 mL 0.2 M glycine (pH 8.0). This solution was allowed to react overnight without stirring at ambient temperature.

PD-Functionalized Antibacterial NR Synthesis.

PD was deposited onto gold NRs. 500 µL of gold NR suspension was centrifuged and resuspended in 1 mL of 10 mM TRIS buffer (pH 8.5). Dopamine hydrochloride was added to a final concentration of 0.555-1.11 mM and sonicated for 30 minutes to form PD-NRs. To incorporate silver into the PD-layer surrounding gold NRs, 0-300 µM $AgNO_3$ in ultrapure DI water was added under stirring, and samples were sonicated for 10 minutes. Samples were centrifuged at 9000 rpm for 10 minutes, and supernatant solution was decanted. To immobilize the antibodies, 12.5 µL of the 0.1 mg/ml antibody solution was added to NR suspensions and sonicated for 30 minutes, and then 10 µL 1 mg/ml mPEG-SH (pH 8.5) was added and sonicated for 30 minutes to backfill the PD layer with passivating polymers. Six distinct formulations of the PD-NRs, with and without silver (Ag), and with and without one of the two antibodies (Ab) were used in subsequent studies (described as PEG-NRs, PEG-Ag—NRs, Ab-NRs, and Ab-Ag—NRs; see FIG. 19 for a schematic representation).

Optical Spectroscopy.

A Hitachi (Hitachi City, Japan) U-2010 Spectrophotometer was used to acquire optical spectra in a two-beam geometry. 10 mM TRIS buffer (pH 8.5) was used for the reference beam. Spectral scans were performed at a resolution of 1 nm over the 200-1000 nm range of wavelengths in the UV-Visible-NIR region of the spectrum.

Electron Microscopy.

Pelleted NRs (54) were deposited on EM grids (Ted Pella, Redding, Calif.) and allowed to air dry. Transmission EM (TEM), Z-contrast EM (ZCEM), secondary EM (SEM), and energy dispersive X-ray spectroscopy (EDS) spectral imaging were performed on a Hitachi HD-2300 Ultra High Resolution FE-STEM (Hitachi City, Japan). The beam was operated at 200 kV.

Quantitative Photothermal Heating Experiments.

NR samples were centrifuged and resuspended in 50 µL ultrapure deionized ultrapure water. Samples were irradiated with a 50 mW NKT photonics SUPERK™ Versa laser source (650 nm-850 nm) with a 1 mm spot size for 10 minutes. NR suspension temperature was monitored with a Luxtron 1652 Industrial Fluoroptic Thermometer (Lambda Photometrics; Hertfordshire, UK) with a fiber optic thermocouple STF (Shanghai Thermostat Factory) probe designed for harsh environments.

Bacterial Assays.

S. epidermidis and E. coli were grown overnight in Tryptic soy and Luria-Bertani growth media, respectively, under shaking at 37° C. 1 mL of the bacterial suspension was centrifuged at 4600 rpm at 4° C. for 5 minutes, the supernatant decanted, cell pellets were resuspended in 3 mL 0.85% NaCl solution, and the process was repeated 3 times. 1 mL of the cell suspension ($10^9$ CFU/mL) was added to 40 µL PEG-NR, PEG-Ag—NR, Ab-NR, or Ab-Ag—NR pellets, incubated under shaking for 20 minutes at 37° C., and then centrifuged at 2000 rpm at 4° C. for 5 minutes. Supernatant was removed, and the cell pellets were resuspended in 50 µL sterile 0.85% NaCl solution. 5-10 µL were placed onto a glass side and imaged with an optical coherence tomography (OCT) system. Photothermal treatments were performed on 5 µL of the cell suspension placed in a 600 µL eppendorf tube, which were irradiated with 50 mW NKT photonics SUPERK™ Versa laser source (650 nm-850 nm) with a 1 mm spot size for 10 minutes. Cells were stained with SYTO® 9 green fluorescent nucleic acid stain and propidium iodide (Invitrogen) according to manufacturer's specifications, and imaged with an epifluorescent microscope. Cell viability was quantified by counting individual numbers of live and dead cells with ImageJ software (6 fields of view per condition, ~100 cells per field of view).

Inductively Coupled Plasma Optical Emission Spectrometry (ICP-OES).

2 mL of PD-coated nanorod (PD-NR) suspension was centrifuged. 100 µL of the supernatant was added to 200 µL 70% nitric acid and sonicated for 4 hours at 22° C. in a Branson 2510 sonicator. The remaining supernatant was removed, and the pellet was resuspended in 50 µL. 5.5 µL was added to 200 µL 70% nitric acid and sonicated for 4 hours. Pure water was added to bring the total volume to 4 mL samples. Ag concentration was determined in a Varian VISTA-MPX ICP-OES Spectrometer (Varian, Inc. Santa Clara, Calif.) using a calibration curve constructed from 0.1, 0.5, 1, 2, 5, and 10 ppm silver standards (dissolved in 2% nitric acid). Gold NR concentration was quantified by methods described previously (see Example 2).

X-Ray Photelectron Spectroscopy (XPS).

NR samples were centrifuged, and pellets were deposited onto silicon oxide surfaces and allowed to dry. An Omicron (Taunusstein, Germany) XPS/ESCA Probe was used to acquire spectra. A survey scan over 0-1100 eV binding energy range with 0.5 eV resolution was performed. Higher 0.04 eV resolution spectra were acquired on the identified Au 4 $f_{7/2}$ and 4 $f_{5/2}$, Ag 3d, C 1s, O 1s, and N 1s peaks. The binding energy spectral ranges were 82.5-90.5 eV for Au, 364.0-380.0 eV for Ag, 283.5-289.02 eV for C, 530.5-536.5 for O, and 395.0-405.0 eV for N. Spectra were calibrated to the C—C peak, located at 284.5 eV.

Results.

Synthesized gold NRs were characterized by strong longitudinal SPRs centered near 800 nm and less intense transverse SPRs near 520 nm. Deposition of PD onto gold NR surfaces caused a slight red-shift in the longitudinal SPR (FIG. 20a), and the coating was visible under secondary electron microscopy (FIG. 20b). Within seconds of silver addition, a pronounced color change occurred in the suspension. The observed colors stabilized within 10 minutes, which included red, yellow, green, purple, and orange (FIG. 21a), from low to high silver concentration respectively. This color change was accompanied by a pronounced increase in intensity, sharpening, and blue-shift of the longitudinal SPRs (FIG. 21b). Addition of 50, 100, 200, and 300 µM silver nitrate to a PD-NR suspension with an initial longitudinal SPR extinction peak centered at 804 nm shifted the peak to 693 nm, 629 nm, 565 nm, and 531 nm, respectively. The blue-shift observation was independent of the initial wavelength of the longitudinal SPR (data not shown). A strong optical backscattering peak that was red-shifted compared to overall extinction was observed from these metal NRs (FIG. 21c).

Electron microscopy was performed to confirm the deposition of silver onto PD-NRs. Gold NR core-silver shell NP morphologies were evident under TEM (FIG. 22a) and ZCEM (FIG. 22b), and average coating thicknesses between 1 and 8 nm were tuned by the concentration of silver added. Gold and silver were spatially identified on a single NP with EDS (FIG. 23), revealing a gold rod core (red) surrounded by a silver shell (teal), as evidenced by the increase in the Ag/Au ratio in the EDS spectra, which was confirmed by ICP-OES (FIG. 24). A significantly higher Ag 3d signal was observed in XPS spectra of samples incubated with silver compared to nonmetalized counterparts (FIG. 25).

The photothermal properties of the NR suspensions were characterized upon irradiation, and substantial heating occurred in NR suspensions compared to water controls (FIG. 26). PEG-NR suspensions increased from 20.6° C. to 24.2° C. within 1 minute, rising to 41.9° C. in 5 minutes, and reached a steady state condition of 44° C. after 8 minutes of irradiation. Addition of silver into the PD layer moderately decreased the temperature increase compared to PD-NRs without silver incorporation. These NR suspensions increased from 20.6° C. to 22.1° C. in the first minute of irradiation, rose to 38.5° C. after 5 minutes, and reached a steady state condition of 40° C. in 8 minutes. Water controls irradiated identically only increased to 21° C. in the first minute, reached 24° C. in 5 minutes, and did not significantly increase over the next five minutes of irradiation.

To provide bacterial strain specificity to PD-NRs, antibodies that target lipoteichoic acid in gram-positive bacterial cell walls or endotoxin on gram-negative cell walls were immobilized onto the PD layer. Red-shifts of the NR SPRs occurred upon initial antibody functionalization, which matched previously reported results, after which no statistical shift in SPRs occurred in 0.85% salt solutions over 4 hours (FIG. 27). 87% and 54% of the SPR intensity of Ab-Ag—NRs and Ab-NRs preserved, respectively. A 7 nm shift was detected in Ab-NR SPRs over 24 hours, but no shift was detected in Ab-Ag—NR SPRs over the same time period.

Biomimetic antibacterial metal NRs were incubated with gram-negative E. coli and gram-positive S. epidermidis bacterial cells and characterized with OCT (FIG. 28). After incubation with antibody-functionalized NRs and centrifugation to remove unbound NRs, bacterial pellets were visibly darkened; cell pellets incubated with PEG-functionalized NR controls were significantly less intensely stained. Under OCT, both E. coli and S. epidermidis cell suspensions exhibited increased brightness and contrast after incubation with antibody-functionalized NRs as compared to PEG-functionalized NRs, and silver deposition onto NRs further increased both the brightness and contrast of the OCT images (FIG. 28). Features from the tail of the SPR were detected from cell pellets, particularly with *S. Epidermidis* (FIG. 29a), implying co-localization of cells and NRs.

Photothermal therapy was performed successfully on gram-positive *S. epidermidis* and gram-negative *E. coli* (FIGS. 30, 31, and 32). With regard to *S. epidermidis*, multiple components were necessary to provide killing. Incubation with PEG-NRs, PEG-Ag—NRs, and Ab-NRs, followed by irradiation with 50 mW broadband light did not produce therapeutic responses, yielding cell viabilities of 90%, 91%, and 94%, respectively, not significantly different than untreated controls. However, strong synergistic therapeutic responses were observed between Ab-Ag—NRs and light irradiation (FIG. 30). More specifically, only NRs coated in silver and functionalized with antibodies specific to lipoteichoic acid that were also irradiated with light provided robust *S. epidermidis* killing. With this treatment, cell viability was reduced to 10%.

The synergistic effects from silver, antibody, and light were less obvious but still observed in the case of *E. coli* (FIG. 31). PEG-NRs were moderately toxic to *E. coli* cells (73% viability), and their viability was reduced to 63% when irradiated with light. Incubation with PEG-Ag—NRs reduced *E. coli* viability to 58%, and addition of irradiation provided a robust effect, reducing viability to 15%. NRs functionalized with antibodies (Ab-NRs) that bind to endotoxins aggregated into cell clusters, and cell viability was reduced to 46% when irradiated with light. Addition of silver into the PD layer surrounding the NRs enhanced the toxicity of the irradiation-induced effect, killing 92% of the bacteria in solution (8% viability).

Discussion.

Photothermal therapeutic agents composed of gold NRs coated with PD, silver, and antibacterial antibodies were synthesized (FIG. 18). In Examples 1 and 2, PD was deposited onto gold NRs to provide a versatile catecholamine chemical surface for further functionalization. In this example, these PD-NRs (FIG. 20) were employed as antibacterial agents by incorporating silver and antibodies into the PD primer layer to target bacterial cell surfaces for silver-based antibacterial photothermal therapy.

In order to provide antibacterial properties to the NIR-active gold NRs, silver was deposited onto NRs. Silver binds DNA, interferes with enzymes, and binds to cell surface molecules, making it a multifunctional antimicrobial that has had therapeutic success against otherwise antibiotic resistant bacteria. The antibacterial coating was deposited by the addition of silver nitrate into basic PD-NR suspensions. We hypothesize that upon addition of silver nitrate, the catechols in the PD layer, which reduce gold and silver ions in basic solutions, reduce silver ions into metal silver embedded in a PD matrix surrounding gold NRs. This was confirmed by the successful detection of silver on gold NRs with EM (FIG. 22), EDS spectral imaging (FIG. 23), and ICP-OES (FIG. 24), as well as the detection of metallic silver in XPS (FIG. 25). The thickness of the silver coatings, between 1 and 8 nm, was easily controlled by varying the amount of silver nitrate added to the NR solution.

Silver deposition on gold NRs also caused a distinct suspension color change associated with SPR blue-shifting and sharpening (FIGS. 21 and 23). By controlling the thickness of the silver coating, the longitudinal SPR extinction peak wavelength could be tuned between 520 nm and 860 nm. This SPR tuning also implies that the silver-containing PD layer has conductive properties, and that silver doping provides an avenue to tune the band-gap properties of melanin-like semiconducting PD interfaces. This SPR control is useful in solving the broader challenge of matching the optical properties of targeted metal NPs with light sources for imaging and photothermal therapy. Tissue penetration is a major limitation of in vivo optical imaging techniques that can be maximized by using NIR light, however higher resolution imaging of tissue surfaces can be acquired with shorter wavelength visible light. Importantly, the metal PD-NRs described here can be assembled such that their optical properties are optimized for either application. Peak sharpening was also observed by silver shell deposition, associated with plasmonic focusing, an effect that increases their potential as contrast agents.

Increased scattering also occurs at the silver-gold interface of the Ag—NRs (FIG. 21c), and can be detected in optical diagnostic imaging techniques like dark field microscopy and OCT. Indeed the increased brightness and SPR spectral features observed in OCT images of cell samples incubated with Ab-Ag—NRs (FIGS. 28 and 29) is due to the backscattering (FIG. 21c) from the metal NRs bound to cells. Silver deposition also increases the magnitude of light extinction per NR (FIG. 21b). Taken together, the addition of silver to the NRs makes them antibacterial, plasmonically tunable, and more efficient detection and treatment agents. However, in order for photothermal and silver treatments to work efficaciously the NR must be in close proximity with the bacteria.

To adhere metal NRs directly to the bacterial cell walls, antibacterial antibodies specific to components in the membrane can be immobilized to PD-NR surfaces by reaction under mildly basic conditions. To target gram-negative cells, antibodies for endotoxin were conjugated to NRs; for gram-positive cells, antibodies specific to lipoteichoic acid were immobilized. SPR red-shifts were detected upon functionalization in both PD-NRs and Ag—NRs, indicating a thicker coating on NRs, results similar to those described in the previous examples. It is hypothesized that amines in the antibodies covalently react with the quinones of the PD layer. With the addition of antibodies along with PEG, the NRs were stable in salt solutions over a period of 4 hours (FIG. 27), with SPRs of Ab-Ag—NRs not shifting over 24 hours, indicating their stability in saline environments.

OCT imaging confirmed antibody-functionalized NR targeting to bacterial cells. After incubation with antibody-functionalized NRs and washing, cell suspensions of both *E. coli* and *S. epidermidis* were significantly brighter compared to control cells incubated with PEG-NRs (FIG. 28). This results from the increased number of NRs present in the sample, due to enhanced binding of NRs to bacterial cells, providing bright backscattering contrast in OCT. Additionally, due to the increased scattering from the gold-silver interface, Ab-Ag—NRs were significantly brighter under OCT compared to Ab-NRs. This increased brightness and contrast upon binding can be used for detection of specific strains of bacteria with particular membrane components with high sensitivity and signal-to-noise ratio. While two specific antibacterial antibodies for endotoxin and lipoteichoic acid were used in this study, other antibodies and smaller targeting molecules like peptides and antibody fragments can be integrated into the described PD-based strategy.

Once targeted to bacterial cells, NRs can be irradiated with light to produce a potent therapeutic response. The SPR of the metal NRs causes high absorption of light energy, leading to substantial heating (FIG. 26). In this study, substantial bulk temperature rises between 20-25° C. from baseline were detected upon irradiation of NRs, which correspond to even higher local temperature increases from NR surfaces. Further, PD is similar in structure to melanin, a natural photopigment evolved to protect organisms from light damage by converting light energy to heat, which may enhance the conversion of light to heat. Since the NRs are targeted to the cell surface, the extreme heating upon irradiation locally disrupts cellular membranes, resulting in effects that can range from moderate swelling to pressure induced cavitation from bubbles formed by water evaporation and metal NP explosion.

Synergistic therapeutic effects occurred between the presence of silver and light irradiation in the bacterial cell viability assays. Since silver actually decreased NR photothermal potential (FIG. 26), it is hypothesized the enhanced toxicity is due to release of silver upon irradiation. Potentially, as the temperature rises, the PD layer surrounding the NR can become damaged through denaturation or destabilized through other effects such as vibrations or local water evaporation, which can produce silver release in ionic or particulate form. Once released, silver provides multiple therapeutic effects, including binding to DNA, respiratory enzymes, and cell surface molecules and receptors.

Gram-negative E. coli cells were efficiently killed by irradiation after incubation with metal NRs (FIG. 31), and synergistic responses were observed between the multiple components of the therapy. Light-activated toxicity was detected even when incubated with PEG-NRs, a phenomenon significantly enhanced with addition of silver into the system, presumably due to silver release upon irradiation. NRs targeted with antibodies and irradiated were more toxic compared to PEG controls due to the binding of the NRs to the cell membrane by the conjugated antibody. NRs coated in silver and functionalized with antibodies provided greater killing when coupled with irradiation than any other formulation. This implies that binding the particles to the cell surface with antibodies and irradiating them with light, to simultaneously cause membrane damage and release silver, provides multifunctional photothermal therapy.

Interestingly, S. epidermidis was evidently more resistant to light treatment in the presence of NRs (FIG. 30). Distinct from E. coli, the presence of the NR, silver, antibody, and the use of irradiation were all necessary to efficiently kill S. epidermidis cells in solution. It is hypothesized that the thick peptidoglycan layer in the cell walls of gram-positive bacteria like S. epidermidis, which is not present in gram-negative counterparts like E. coli, protects against the extreme heating that occurs from cell-wall-bound NRs upon irradiation. However, by combining a NIR active metal NP, silver, and antibacterial antibodies with PD, the multifunctional antibacterial agents bind to lipoteichoic acid embedded in the peptidoglycan layer with antibodies, then photothermally damage the cell membrane while simultaneously releasing silver when irradiated with light to kill the cells.

Metal NPs have SPR material properties that can be harnessed for a variety of biomedical applications when their surfaces are biofunctionalized, including photothermal treatment of bacterial cells. Natural bioadhesives of the marine mussel have evolved to adhere to any material in harsh, salty environments, and catecholamine molecular layers inspired by mussel adhesive proteins have the flexible chemical repertoire necessary to provide a robust multifunctional interface between metal NP surfaces and organic molecules like PEG and antibodies, which are a central weapon in the human immune system. By coupling their functionality with the electromagnetic properties of metal NPs through biomimetic adhesives, hybrid biometallic nanomaterials can be engineered to treat resistant diseases like cancer and bacterial infections with novel, individualized therapies that integrate NP-enhanced photothermal therapy with cell surface targeting.

The invention is not limited to the embodiments set forth herein for illustration, but includes everything that is within the scope of the claims. Furthermore, all references cited herein are hereby incorporated by reference in their entirety and for all purposes as if fully set forth herein.

We claim:

1. A method for treating cancer comprising administering to a patient having cancer cells one or more nanoparticles comprising:
    (a) a metallic core consisting essentially of gold and having a length along each axis of from 1 to 100 nanometers;
    (b) a coating comprising polydopamine disposed on at least part of the surface of the metallic core; and
    (c) one or more cetuximab anti-cancer cell surface receptor antibodies;
    whereby the one or more nanoparticles target the cancer cells and the cancer is effectively treated, and wherein the cancer is selected from the group consisting of metastatic colorectal cancer, head and neck cancer, and epidermal growth factor receptor (EGFR)-expressing breast cancer.

2. The method of claim 1, wherein the one or more nanoparticles further comprise an additional anti-cancer agent bound to the coating.

3. The method of claim 2, wherein the anti-cancer agent is a proteasome inhibitor.

4. The method of claim 1, further comprising the step of exposing the nanoparticles to light.

5. A method for treating cancer, the method comprising:
    administering to a patient having cancer cells one or more nanoparticles comprising:
    (a) a metallic core consisting essentially of gold and having a length along each axis of from 1 to 100 nanometers;
    (b) a coating comprising polydopamine disposed on at least part of the surface of the metallic core; and
    (c) one or more cetuximab anti-cancer cell surface receptor antibodies; and
    exposing the nanoparticles to light, whereby the one or more nanoparticles target the cancer cells and the cancer is effectively treated, and wherein the cancer is selected from the group consisting of metastatic colorectal cancer, head and neck cancer, and epidermal growth factor receptor (EGFR)-expressing breast cancer.

* * * * *